(12) United States Patent
Hyer et al.

(10) Patent No.: US 10,463,840 B2
(45) Date of Patent: Nov. 5, 2019

(54) COMPLIANT CATHETER ADAPTER HAVING SELF-SLITTING NEEDLE

(71) Applicant: Becton, Dickinson and Company, Franklin Lakes, NJ (US)

(72) Inventors: Daniel Kirk Hyer, Layton, UT (US); Christopher Maul, Columbus, NE (US); Eric Davis, Saratoga Springs, UT (US); Bin Wang, Sandy, UT (US); Carl Ellis, Sandy, UT (US); Corey Christensen, Salt Lake City, UT (US); Jonathan Karl Burkholz, Salt Lake City, UT (US); Bart D. Peterson, Farmington, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 205 days.

(21) Appl. No.: 15/286,223

(22) Filed: Oct. 5, 2016

(65) Prior Publication Data
US 2017/0120001 A1    May 4, 2017

Related U.S. Application Data

(60) Provisional application No. 62/247,596, filed on Oct. 28, 2015, provisional application No. 62/296,383, (Continued)

(51) Int. Cl.
*A61M 25/06* (2006.01)
*A61M 5/32* (2006.01)
(Continued)

(52) U.S. Cl.
CPC ...... *A61M 25/0637* (2013.01); *A61M 5/3286* (2013.01); *A61M 5/3291* (2013.01);
(Continued)

(58) Field of Classification Search
CPC .. A61M 25/01; A61M 5/3286; A61M 5/3291; A61M 25/0043; A61M 25/0097; A61M 25/0606
(Continued)

(56) References Cited

U.S. PATENT DOCUMENTS 5,059,186 A * 10/1991 Yamamoto ......... A61M 25/0111
600/435
5,531,720 A 7/1996 Atkins
(Continued)

FOREIGN PATENT DOCUMENTS

EP    0 732 120 A1    9/1996
EP    2 044 970 A1    4/2009
(Continued)

*Primary Examiner* — Phillip A Gray
(74) *Attorney, Agent, or Firm* — Kirton & McConkie; Craig Metcalf; Kevin Stinger

(57) ABSTRACT

A self-slitting open lumen cannula may be used with catheter adapters to reduce manufacturing complexity and costs, as well as improve the safety of the catheter adapters against fluid leakage. The open lumen cannula may also include one or more notches to facilitate flashback visualization. The catheter adapters may further include a catheter adapter body formed of a compliant material that houses one or more compression resistant septa with at least one lumen formed by the proximal end of the needle during a self-slitting process as the catheter adapter is assembled. The compression resistant septum may also be coupled to a compression cap that imparts a radial compression force on the one or more compression resistant septa such that the at least one lumen narrows and seals when the cannula is removed.

20 Claims, 16 Drawing Sheets

Related U.S. Application Data filed on Feb. 17, 2016, provisional application No. 62/247,599, filed on Oct. 28, 2015, provisional application No. 62/247,617, filed on Oct. 28, 2015, provisional application No. 62/247,607, filed on Oct. 28, 2015, provisional application No. 62/247,621, filed on Oct. 28, 2015, provisional application No. 62/247,624, filed on Oct. 28, 2015, provisional application No. 62/247,626, filed on Oct. 28, 2015, provisional application No. 62/296,385, filed on Feb. 17, 2016.

(51) Int. Cl.
*A61M 39/06* (2006.01)
*A61M 25/00* (2006.01)

(52) U.S. Cl.
CPC .... *A61M 25/0097* (2013.01); *A61M 25/0606* (2013.01); *A61M 25/0693* (2013.01); *A61M 39/06* (2013.01); *A61M 2039/062* (2013.01)

(58) Field of Classification Search
USPC .......................................................... 604/167
See application file for complete search history.

(56) References Cited

U.S. PATENT DOCUMENTS 5,810,780 A * 9/1998 Brimhall ........... A61M 25/0693
604/167.02
D458,678 S 6/2002 Cindrich

FOREIGN PATENT DOCUMENTS

| | | |
|---|---|---|
| GB | 2508466 A | 6/2014 |
| WO | 02/096495 A2 | 12/2002 |
| WO | 2004/032995 A2 | 4/2004 |
| WO | 2006/067660 A1 | 6/2006 |
| WO | 2007/050788 A2 | 5/2007 |

* cited by examiner

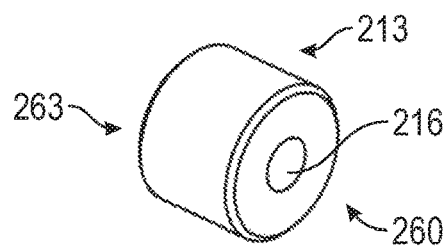
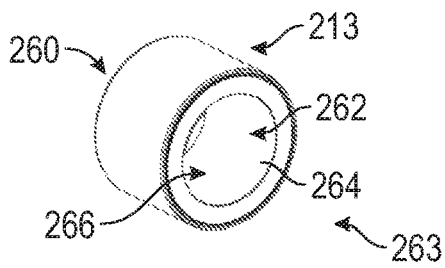
FIG. 3A  FIG. 3B
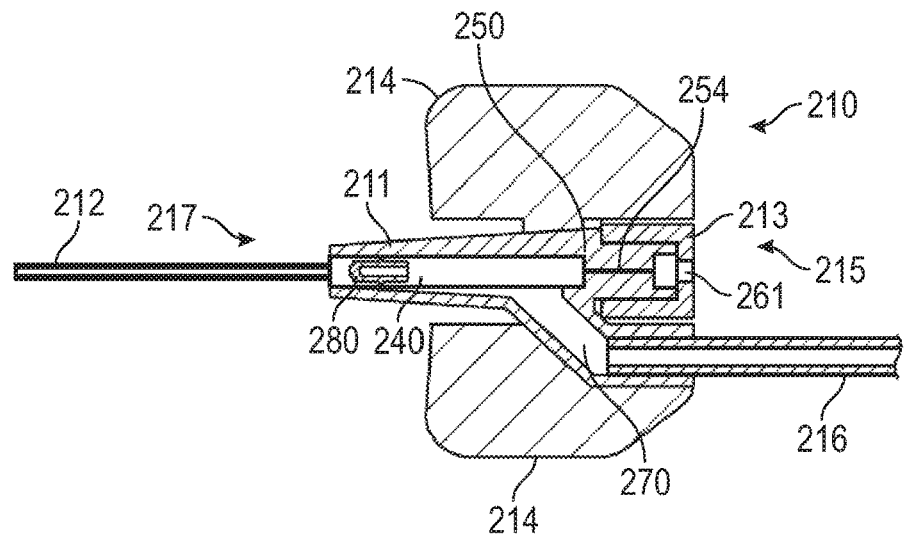
FIG. 3C
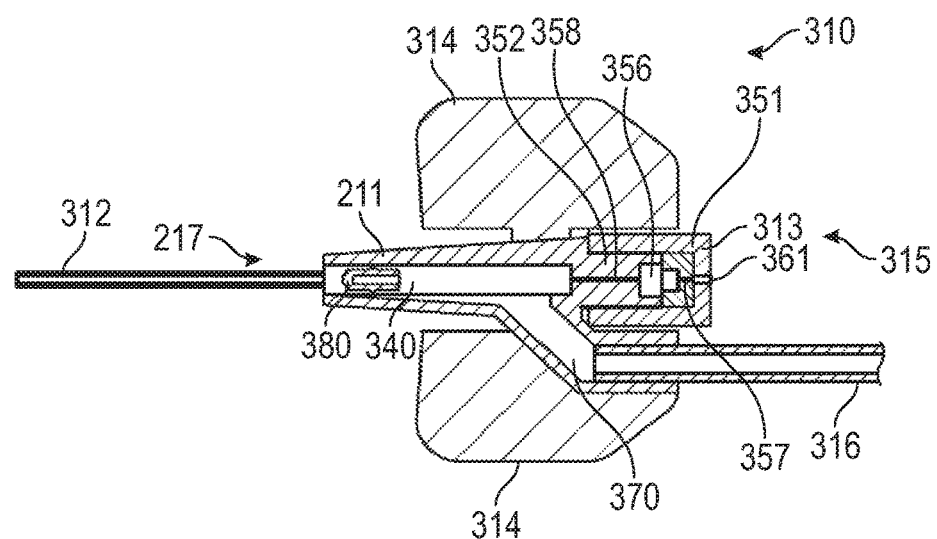
FIG. 3D

COMPLIANT CATHETER ADAPTER HAVING SELF-SLITTING NEEDLE

RELATED APPLICATIONS

This application claims the benefit of U.S. Provisional Patent Application No. 62/247,596, which was filed on Oct. 28, 2015, U.S. Provisional Patent Application No. 62/296,383, which was filed on Feb. 17, 2016, U.S. Provisional Patent Application No. 62/247,599, which was filed Oct. 28, 2015, U.S. Provisional Patent Application No. 62/247,617, which was filed on Oct. 28, 2015, U.S. Provisional Patent Application Ser. No. 62/247,607, which was filed Oct. 28, 2015, U.S. Provisional Patent Application Ser. No. 62/247,621, which was filed Oct. 28, 2015, U.S. Provisional Patent Application Ser. No. 62/247,624, which was filed Oct. 28, 2015, U.S. Provisional Application No. 62/247,626, which was filed on Oct. 28, 2015, and U.S. Provisional Application No. 62/296,385, which was filed on Feb. 17, 2016, each of which is incorporated herein by reference in their entirety.

FIELD OF THE INVENTION

The present disclosure relates to catheters. More specifically, the present disclosure relates to compliant catheter adapters including self-slitting needles that may facilitate manufacturing and assembly processes.

BACKGROUND OF THE INVENTION

Intravascular (IV) catheters may be used to infuse fluids into the vascular system of a patient, such as saline solution, various medicaments, total parenteral nutrition, etc. IV catheters may also be used to withdraw blood from the patient, or to monitor various parameters of the patient's vascular system.

Peripheral IV catheters may be relatively short (typically on the order of about two inches or less in length). The most common type of IV catheter is an over-the-needle peripheral IV catheter. As its name implies, an over-the-needle IV catheter is mounted over an introducer needle having a sharp distal tip. At least the distal portion of the catheter tightly engages the outer surface of the needle to prevent "peelback" of the catheter and thus facilitates insertion of the catheter into the blood vessel. The distal tip of the introducer needle may extend beyond the distal tip of the catheter with the bevel of the needle facing up away from the patient's skin.

The catheter and introducer needle assembly may be inserted at a shallow angle through the patient's skin into a blood vessel. There are many techniques for inserting such a catheter and introducer needle assembly into a patient. In one insertion technique, the introducer needle and catheter are inserted completely into the blood vessel together. In another technique, the introducer needle is partially withdrawn into the catheter after the initial insertion into the blood vessel. The catheter is then threaded over the needle and inserted completely into the blood vessel.

In order to verify proper placement of the catheter in the blood vessel, the clinician may confirm that there is a flashback of blood in a flashback chamber. The flashback chamber is typically formed as part of a needle component or needle hub. Alternatively, the introducer needle could include a notch or opening formed along a distal portion thereof so that the blood flashback can be observed in the annular space between the introducer needle and the catheter when the catheter is transparent, or at least translucent. The clinician may then withdraw the introducer needle, leaving the catheter in place, and/or attach an appropriate device to the catheter. Such a device can include a fluid delivery device, a PRN, a deadender cap, a blood pressure monitoring probe, etc.

One common method of administering fluids into a patient's blood flow is through an intravenous delivery system. Intravenous delivery systems may include a liquid source such as a liquid bag, a drip chamber used to determine the flow rate of fluid from the liquid bag, tubing for providing a connection between the liquid bag and the patient, and an intravenous access unit, such as a catheter, that is positioned intravenously in the patient. The catheter may include a catheter adapter with one or more connectors or ports that are configured to allow "piggybacking" of intravenous delivery systems which may be used to administer medicine, among other functions.

Although typical IV catheter and introducer needle assemblies generally perform their functions satisfactorily, they do have certain drawbacks. For example, the procedure for properly placing a catheter into a patient's blood vessel can result in a significant amount of blood leakage from the catheter between the initial venipuncture and the time that an appropriate device is connected to the catheter. This blood leakage is problematic because of potential contamination to a clinician from an infected patient. This is especially worrisome because of diseases such as Acquired Immune Deficiency Syndrome ("AIDS") which can be transmitted by the exchange of body fluids from an infected person to another person.

In order to minimize blood leakage, infusate leakage, and/or air aspiration, a self-sealing septum may be placed in the proximal end of the catheter adapter. The septum allows the introducer needle to extend through the septum and the catheter to allow the catheter to be placed into a patient's blood vessel. In addition, the septum allows the clinician to withdraw the introducer needle from the catheter and the septum, which then closes after the introducer needle has been completely withdrawn from the catheter hub. This arrangement may minimize blood leakage from the catheter adapter. The use of a septum may significantly increase the force that the clinician needs to exert on the introducer needle in order to withdraw the introducer needle from the catheter. Additionally, if the introducer needle is located in the septum for extended periods of time, the septum may take a compression set about the introducer needle preventing the septum from completely sealing once the introducer needle is withdrawn from the septum. Compression set is a material condition resulting from stress over time causing the material to maintain part or all the deformation caused by an interfacing component, even after that interfacing component is removed. Septum geometry may be designed to minimize compression set to reduce the chance of septum leakage after the introducer needle is removed, as taught in U.S. Patent Application No. US20130218082 which is hereby incorporated by reference herein in its entirety.

Once the catheter has been placed in a patients' vein, and the introducer needle has been removed, the clinician will typically secure the catheter adapter body to the patient's skin to prevent accidental removal of the catheter from the patient's vein. However, catheter adapter bodies are typically formed with rigid materials that do not conform well to the patient's skin and are not comfortable. Moreover, catheter adapter bodies formed of many different materials may be more expensive and difficult to manufacture because of their complexity. Accordingly, there is a need for soft body catheter adapters that better conform to the patient's body, improve patient comfort, and can be more securely affixed to the patient. Moreover, soft body catheter adapters may achieve a reduced cost of manufacture because they may be substantially molded from a single compliant material in an integral fashion, thus reducing the number and/or amount of different materials that may be needed during the manufacturing process.

Prior needle designs typically have distal ends with sharp bevel tips to facilitate penetration of a patients' skin and blood vessels as well as blunt shaped proximal ends that may be coupled to a suitable needle hub during assembly of the catheter system. However, blunt shaped proximal ends typically require that a lumen or slit first be formed in the septum via a "pre-slitting" process in order to allow passage of the proximal end of the needle through the septum for coupling to a suitable needle hub. This "pre-slitting" process increases manufacturing efforts and costs. Moreover, any "off-slit landing" of the proximal end of the needle on the septum during assembly may result in damage to the septum which may lead to fluid leakage.

Additionally, prior needle designs may suffer difficulties during the bonding process of the proximal end of the needle to a suitable needle hub. For example, press fitting a blunt shaped needle proximal end into a needle hub via an interference fit may result in "skiving" the interference region of the hub and crimping and/or gluing the needle proximal end into a needle hub may seal off the cannula of the needle disabling extended blood "flashback" capabilities which may be desirable for continuous vein confirmation (i.e., visualization of blood flowing out of the cannula of the needle as the needle is advanced into the patient's vein).

SUMMARY OF THE INVENTION

In some embodiments, a catheter adapter may include a needle having a proximal end, a distal end, and plurality of notches disposed along the needle between the proximal end and the distal end of the needle configured to facilitate flashback visualization. The proximal end of the needle may also be shaped to facilitate a self-slitting process during assembly of the catheter adapter. The catheter adapter may also include a catheter adapter body which may be formed of a compliant material. The catheter adapter body may have a proximal end, a distal end, and a generally elongate shape formed about a longitudinal axis extending between the proximal end and the distal end of the catheter adapter body. The catheter adapter body may also have an inner chamber with a generally elongate shape formed about the longitudinal axis. The compression resistant septum may also have a lumen formed by the proximal end of the needle during the self-slitting process as the catheter adapter is assembled. The compression resistant septum may be further coupled to a compression cap that imparts a radial compression force on the compression resistant septum such that the lumen narrows and seals when the needle is removed from the lumen.

In other embodiments, a compliant catheter adapter may include a needle having a proximal end, a distal end, and plurality of notches configured to facilitate flashback visualization disposed along the needle between the proximal end and the distal end of the needle. The proximal end of the needle may also be shaped to facilitate a self-slitting process during assembly of the catheter adapter. The catheter adapter may also include a catheter adapter body formed of a compliant material. The catheter adapter body may have a proximal end, a distal end, and a generally elongate shape formed about a longitudinal axis extending between the proximal end and the distal end of the catheter adapter body.

The catheter adapter body may also have an inner chamber with a generally elongate shape formed about the longitudinal axis. The catheter adapter body may further include a first compression resistant septum abutted against a second compression resistant septum. The first compression resistant septum may have a first lumen and the second compression resistant septum may have a second lumen, both of which may be formed by the proximal end of the needle during the self-slitting process as the catheter adapter is assembled. The first and second compression resistant septa may be further coupled to a compression cap that imparts a radial compression force on the first and second compression resistant septa such that the first and second lumens narrow and seal when the needle is removed from the first and second lumens.

In yet other embodiments, a catheter system may include a needle component having a needle hub, a needle coupled to the needle hub, and a grip coupled to the needle hub. The needle may have a proximal end, a distal end, and plurality of notches configured to facilitate flashback visualization disposed along the needle between the proximal end and the distal end of the needle. The proximal end of the needle may also be shaped to facilitate a self-slitting process during assembly of the catheter adapter. The catheter system may also include a compliant catheter adapter having a catheter adapter body formed of a compliant material. The catheter adapter body may have a proximal end, a distal end, and a generally elongate shape formed about a longitudinal axis extending between the proximal end and the distal end of the catheter adapter body. The catheter adapter body may also have an inner chamber with a generally elongate shape formed about the longitudinal axis. The catheter adapter body may further include a compression resistant septum that is formed in the compliant material of the catheter adapter body and disposed toward the proximal end of the catheter adapter body. The compression resistant septum may also have a lumen formed by the proximal end of the needle during the self-slitting process as the catheter adapter is assembled. The compression resistant septum may be further coupled to a compression cap that imparts a radial compression force on the compression resistant septum such that the lumen narrows and seals when the needle is removed from the lumen.

These and other features and advantages of the present disclosure may be incorporated into certain embodiments and will become more fully apparent from the following description and appended claims, or may be learned by the practice of the present disclosure as set forth hereinafter. The present disclosure does not require that all the advantageous features and all the advantages described herein be incorporated into every embodiment.

BRIEF DESCRIPTION OF THE DRAWINGS

Exemplary embodiments of the present disclosure will become more fully apparent from the following description and appended claims, taken in conjunction with the accompanying drawings. Understanding that these drawings depict only exemplary embodiments and are therefore not to be considered limiting of the disclosure's scope, the exemplary embodiments of the present disclosure will be described with additional specificity and detail through use of the accompanying drawings in which:

FIG. 3A is an isometric view of a proximal end of a compression cap, according to one embodiment of the present disclosure;

FIG. 3B is an isometric view of a distal end of the compression cap shown in FIG. 3A;

FIG. 3C is an enlarged cross-sectional side view of the catheter adapter of FIG. 2A without the needle component;

FIG. 3D is a cross-sectional side view of a catheter adapter, according to another embodiment of the present disclosure;

DETAILED DESCRIPTION

Figure 1A:
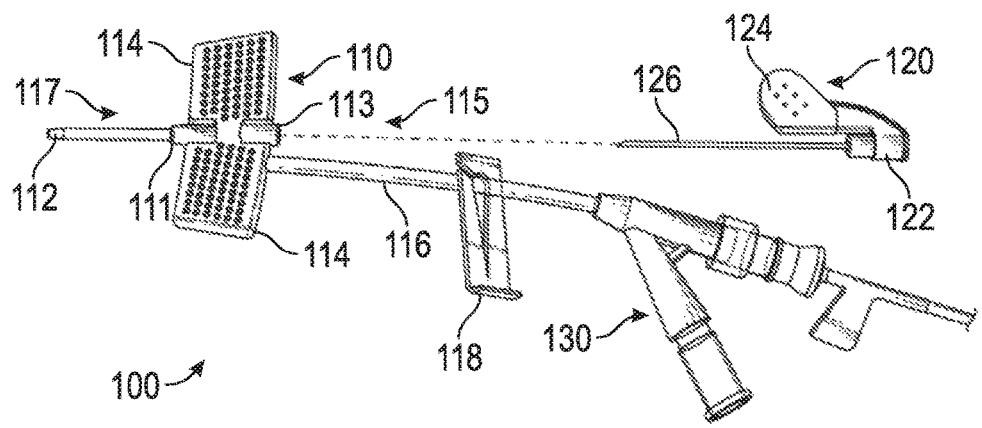
FIG. 1A is an isometric view of an IV catheter set showing a needle component removed from a catheter adapter, according to one embodiment of the present disclosure.

The presently preferred embodiments of the present disclosure may be understood by reference to the drawings, wherein like parts may be designated by like numerals throughout. It will be readily understood that the components of the present disclosure, as generally described and illustrated in the Figures, could be arranged and designed in a wide variety of different configurations. Thus, the following more detailed description is not intended to limit the scope of the present disclosure as claimed, but is merely representative of presently preferred embodiments.

Moreover, the Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Figure 1B:
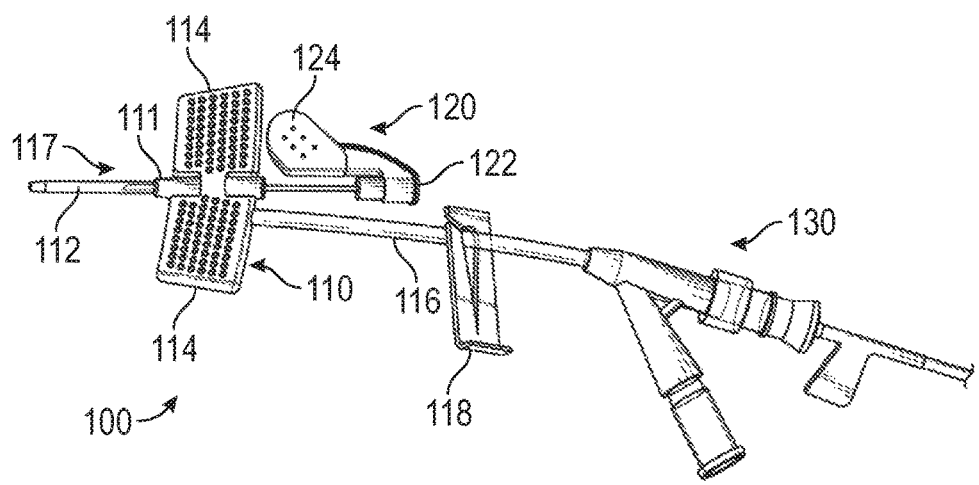
FIG. 1B is an isometric view of the IV catheter set of FIG. 1A with the needle component partially inserted into the catheter adapter.
Figure 1C:
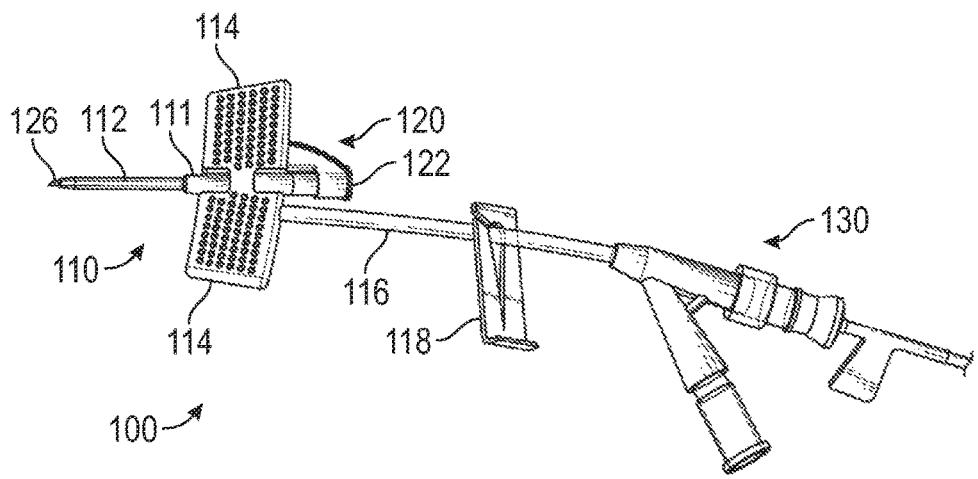
FIG. 1C is an isometric view of the IV catheter set of FIG. 1A with the needle component fully inserted into the catheter adapter.

FIGS. 1A-1C illustrate various isometric views of an IV catheter set 100, according to one embodiment of the present disclosure. The IV catheter set 100 may generally include a compliant catheter adapter 110, a needle component 120, an extension tube 116, a slide clamp 118, and an infusion set 130. FIG. 1A shows the IV catheter set 100 with the needle component 120 removed from the compliant catheter adapter 110. FIG. 1B shows the IV catheter set 100 with the needle component 120 partially inserted into the compliant catheter adapter 110 and FIG. 1C shows the IV catheter set 100 with the needle component 120 fully inserted into the compliant catheter adapter 110.

The compliant catheter adapter 110 may include a catheter adapter body 111 formed of a compliant material. The catheter adapter body 111 may be integrally formed from a compression set resistant elastomeric material including, but not limited to: a thermoplastic elastomer material, a liquid silicone rubber material, a polyisoprene material, and the like. In at least some embodiments, the catheter adapter body 111 may be substantially formed from a single compression set resistant elastomeric material. The compliant catheter adapter 110 may also include a compression cap 113, one or more stabilization members 114, and a catheter lumen 112, as will be discussed in more detail below.

The compliant catheter adapter 110 may include a feature that allows the compliant catheter adapter 110 to be coupled to an extension tube 116. The extension tube 116 may pass through a slide clamp 118 and couple to an infusion set 130. The infusion set 130 may include one or more connectors or injection ports that allow intravenous fluid communication with the patient, as generally known in the art.

The needle component 120 may include a needle hub 122, a grip 124 coupled to the needle hub 122, and an elongate object coupled to the needle hub 122 (such as a needle 126). The needle component 120 may be used to facilitate insertion of the catheter lumen 112 into a vein of a patient (not shown). The embodiment shown in FIG. 1A illustrates a grip 124 having a paddle-like shape or style. However, in other embodiments the grip 124 may include any number of suitable shapes and styles including but not limited to: paddle grips, straight grips, ported grips, etc. For example, FIGS. 2A-2C, 4A-5, and 6B-8 illustrate various examples of grips having different shapes and styles. Likewise, the needle hub 122 may also include any number of suitable shapes and styles.

Figure 2A:
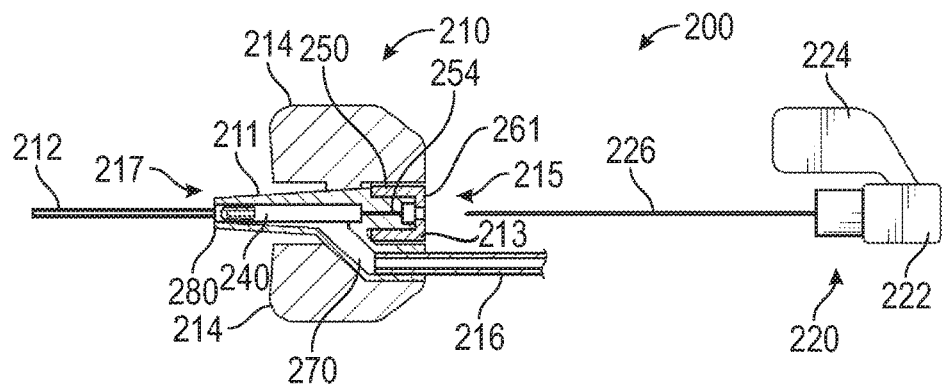
FIG. 2A is a cross-sectional side view of a catheter system with a needle component removed from a catheter adapter, according to another embodiment of the present disclosure.
Figure 2B:
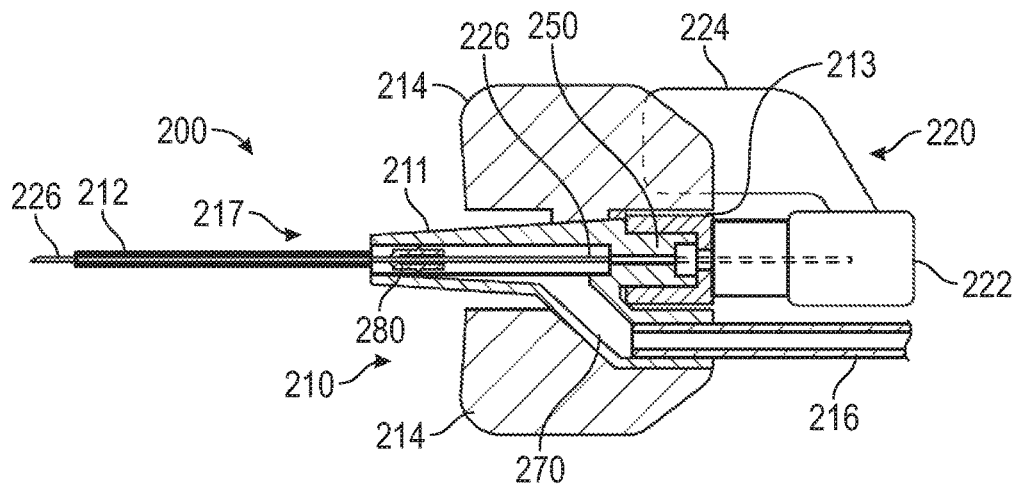
FIG. 2B is a cross-sectional side view of the catheter system of FIG. 2A with the needle component fully inserted into the catheter adapter.
Figure 2C:
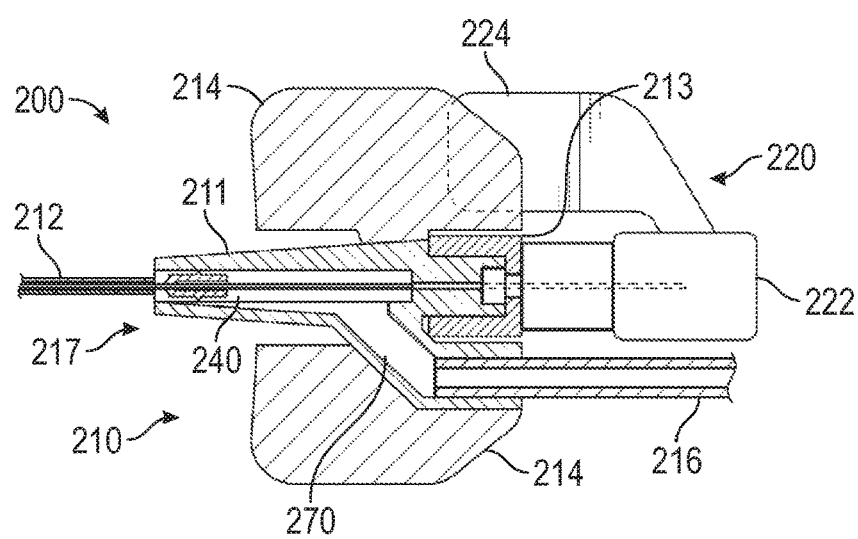
FIG. 2C is an enlarged cross-sectional side view of the catheter system shown in FIG. 2B.

FIGS. 2A-2C and 3C illustrate various views of a catheter system 200 and a compliant catheter adapter 210, according to another embodiment of the present disclosure. FIGS. 3A and 3B illustrate a compression cap 213 that may be used with the compliant catheter adapter 210. FIG. 2A shows a needle component 220 removed from the compliant catheter adapter 210 and FIGS. 2B and 2C show the needle component 220 fully inserted into the compliant catheter adapter 210. FIG. 3C also shows the compliant catheter adapter 210 without the needle component 220. The needle component 220 may include a needle hub 222, a grip 224 coupled to the needle hub 222, and an elongate object, such as a needle 226, coupled to the needle hub 222. The needle component 220 embodiment shown in FIGS. 2A-2C and 3C illustrates a grip 224 having a paddle shape.

Continuing with FIGS. 2A-3C collectively, the compliant catheter adapter 210 may include a catheter adapter body 211 formed of a compliant material. The catheter adapter body 211 may be integrally formed from a compression set resistant elastomeric material such as a thermoplastic elastomer, a liquid silicone rubber, and a polyisoprene. In at least some embodiments, the catheter adapter body 211 may be substantially formed from a single compression set resistant elastomeric material. In at least one embodiment, the catheter adapter body 211 may be integrally manufactured from a compliant material to form an inner chamber 240, a port 270, a compression resistant septum 250 with a lumen 254 extending there through, a catheter wedge 280, and one or more stabilization members 214. The catheter adapter body 211 may also be coupled to any number of non-integral components including, but not limited to: a compression cap 213, a catheter lumen 212, and an extension tube 216.

The catheter adapter body 211 may have a proximal end 215 and a distal end 217. The catheter adapter body 211 may have a generally elongate shape formed about a longitudinal axis of the catheter adapter body 211 (not shown) extending between the proximal end 215 and the distal end 217 of the catheter adapter body 211. The inner chamber 240 may be disposed within the catheter adapter body 211 and also have a generally elongate shape formed about the longitudinal axis of the catheter adapter body 211. The inner chamber 240 may be in fluid communication with the catheter lumen 212. The inner chamber 240 may also include a catheter wedge 280, which may be integrally formed with the inner chamber 240, or may be separately formed from the inner chamber 240 and then coupled to the inner chamber 240. The catheter wedge 280 may be disposed toward the distal end 217 of the catheter adapter body 211 and configured to guide an elongate object into the catheter lumen 212 as the elongate object is inserted through the catheter adapter body 211. For example, the catheter wedge 280 may facilitate and/or guide insertion of the needle 226 into the catheter lumen 212.

The port 270 may be in fluid communication with the inner chamber 240 and configured to receive an extension tube 216. The port 270 shown in FIGS. 2A-2C and 3C has a portion that generally forms a Y-shape in relation to the inner chamber 240 and another portion that generally runs parallel to the inner chamber 240. However, it is understood that the port 270 can be any suitable shape and size including, but not limited to: a Y-shaped port, a T-shaped port, a V-shaped port, a parallel-shaped port, etc.

The one or more stabilization members 214 may be coupled to the catheter adapter body 211 and configured to stabilize the catheter adapter body 211 with respect to a patient (not shown). In at least one embodiment, the one or more stabilization members 214 may be integrally formed with the catheter adapter body 211 such that they are formed from the same compliant material as the catheter adapter body 211. This may allow the catheter adapter body 211 to better conform to the patient's body, improve patient comfort, and improve fixation of the catheter adapter body 211 to the patient after the catheter lumen 212 has been inserted.

The compression resistant septum 250 may be integrally formed in the compliant material of the catheter adapter body 211 and disposed toward the proximal end 215 of the catheter adapter body 211. The compression resistant septum 250 may include a lumen 254 that is formed through the compression resistant septum 250 and configured to receive an elongate object therein, such as the needle 226. In at least one embodiment, the compression resistant septum 250 may be integrally formed of the same compression set resistant elastomeric material as the catheter adapter body 211.

The compression cap 213 may be coupled to the compression resistant septum 250 and the compression cap 213 may be configured to impart a radial compression force to the compression resistant septum 250, such that the lumen 254 of the compression resistant septum 250 narrows and seals when the elongate object is removed from the lumen 254. In at least one embodiment, the compression cap 213 may have a generally cylindrical shape. However, it will be understood that the compression cap 213 may include any number of suitable shapes that are configured to impart a radial compression force. The compression cap 213 may have a proximal end 260 and a distal end 263. The proximal end 260 may have a first aperture 261 formed therein and configured to receive the elongate object there through. The distal end 263 may have a second aperture 262 configured to receive at least a portion of the catheter adapter body 211 and/or at least a portion of the compression resistant septum 250. The compression cap 213 may also include a compression surface 264 that extends intermediate the proximal end 260 and the distal end 263 of the compression cap 213. The compression surface 264 may enclose a hollow portion 266 formed in the compression cap 213. The hollow portion 266 may be configured to receive at least a portion of the compression resistant septum 250 therein, and the compression surface 264 may be configured to impart the radial compression force to the compression resistant septum 250, such that the lumen 254 of the compression resistant septum 250 narrows and seals when the elongate object is removed from the lumen 254. In at least one embodiment, the compression cap 213 is a separate piece that may be coupled to the compression resistant septum 250. However, in other embodiments the compression cap 213 may be integrally formed with the compression resistant septum 250. In yet other embodiments, the compression cap 213 may be coupled to the compression resistant septum 250 through an over-molding manufacturing process.

FIG. 3D shows a cross-sectional side view of a compliant catheter adapter 310, according to another embodiment of the present disclosure. The compliant catheter adapter 310 may include similar features to the compliant catheter adapter 210 of FIGS. 2A-2C and 3C, such as: a catheter adapter body 311 having a proximal end 315 and a distal end 317, a catheter lumen 312, a compression cap 313, one or more one or more stabilization members 314, an extension tube 316, an inner chamber 340, a port 370, and a catheter wedge 380. However, the compliant catheter adapter 310 may also include additional features, such as: a first compression resistant septum 351, a second compression resistant septum 352, a septum chamber 356 intermediate the first compression resistant septum 351 and the second compression resistant septum 352, a first lumen 357, and a second lumen 358.

The first compression resistant septum 351 may be positioned to abut at least a portion of the proximal end 315 of the catheter adapter body 311 and/or the second compression resistant septum 352. The first lumen 357 may be configured to receive an elongate object. The second compression resistant septum 352 may include a second lumen 358 formed there through which may also be configured to receive the elongate object. In at least some embodiments, the second compression resistant septum 352 may be disposed within the inner chamber 340 of the catheter adapter body 311. The second compression resistant septum 352 may be positioned to abut the first compression resistant septum 351 and the septum chamber 356 may be formed between the first compression resistant septum 351 and the second compression resistant septum 352. The compression cap 313 may be configured to couple the first compression resistant septum 351 to the catheter adapter body 311 and/or the second compression resistant septum 352. The compression cap 313 may also be configured to impart a radial compression force to the first compression resistant septum 351 and/or the second compression resistant septum 352 such that the first lumen 357 and the second lumen 358 narrow and seal when the elongate object is removed from the first lumen 357 and the second lumen 358. This configuration may provide additional sealing capabilities and thus, additional safety.

Figure 4A:
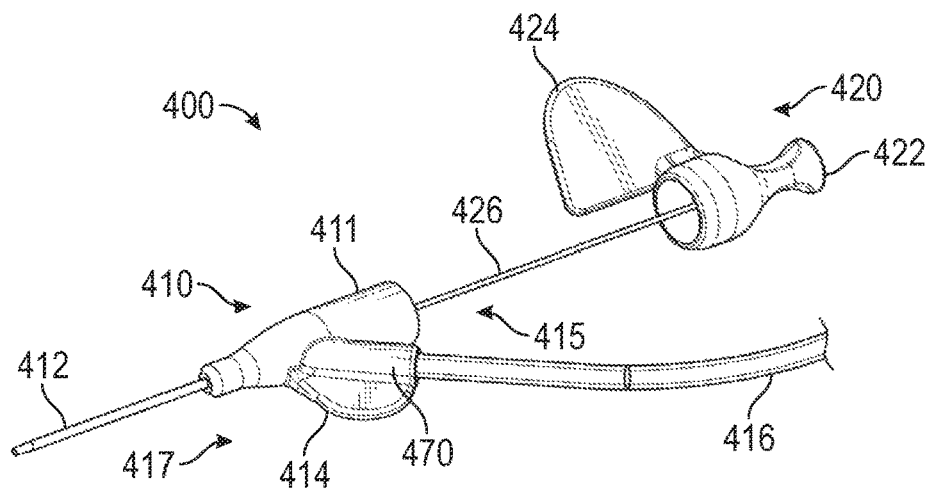
FIG. 4A is an isometric view of a catheter system with a needle component removed from a catheter adapter, according to another embodiment of the present disclosure.
Figure 4B:
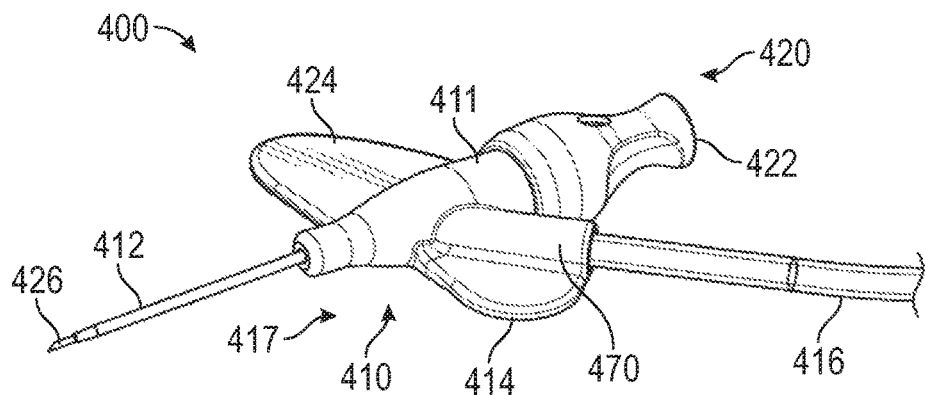
FIG. 4B is an isometric view of the catheter system of FIG. 4A with the needle component fully inserted into the catheter adapter and rotated to a first position.
Figure 4C:
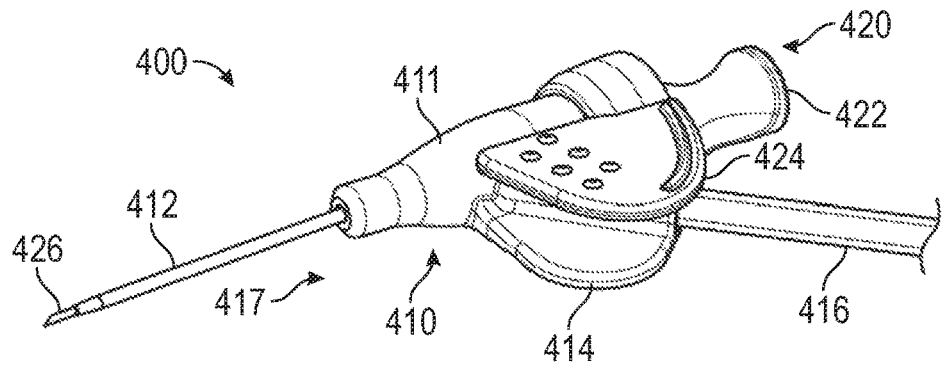
FIG. 4C is an isometric view of the catheter system of FIG. 4A with the needle component fully inserted into the catheter adapter and rotated to a second position.
Figure 5:
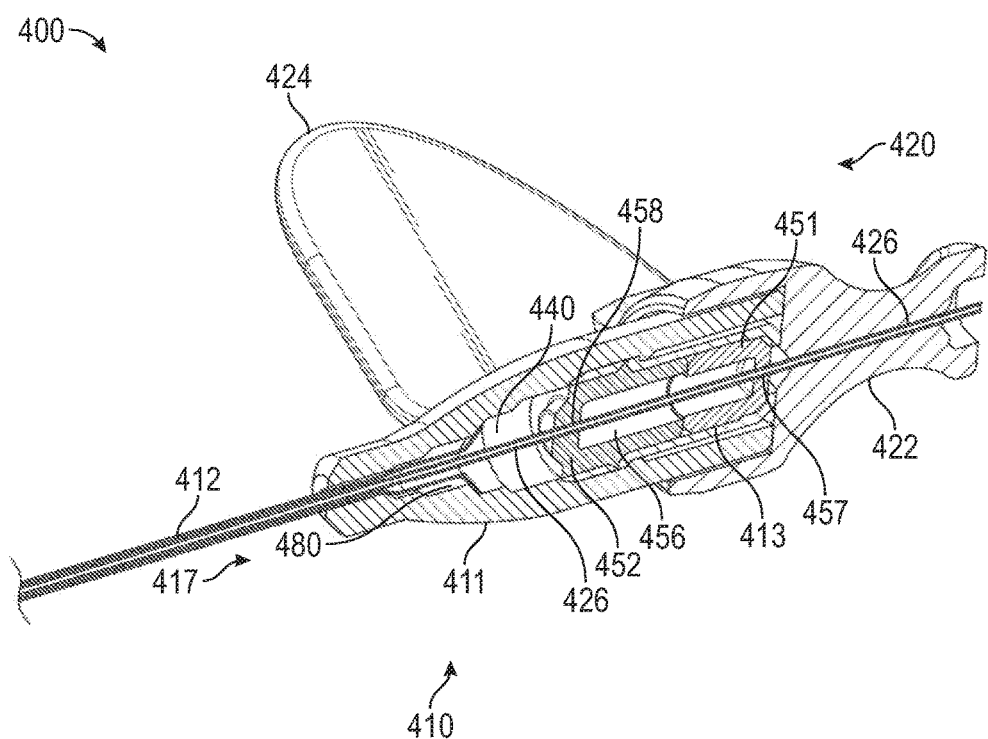
FIG. 5 is a cross-sectional isometric view of the catheter system of FIG. 4B.
Figure 6A:
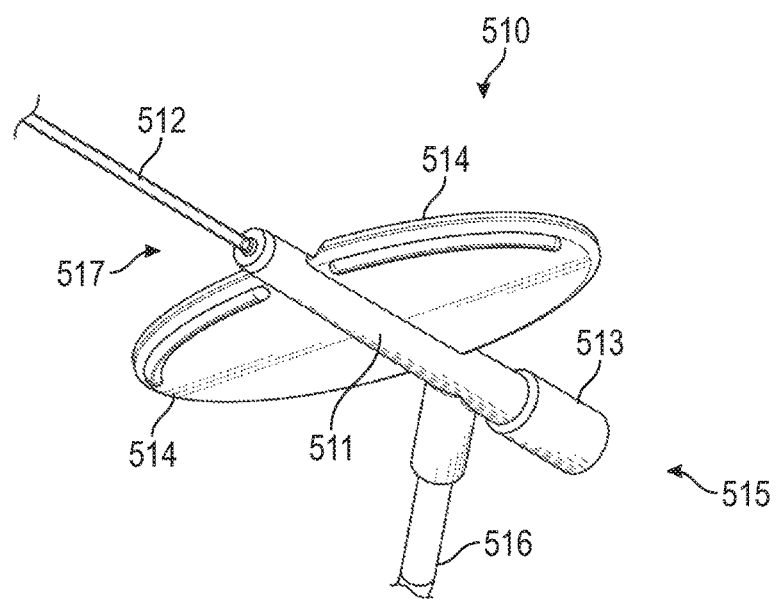
FIG. 6A is an isometric bottom view of a catheter adapter, according to another embodiment of the present disclosure.
Figure 6B:
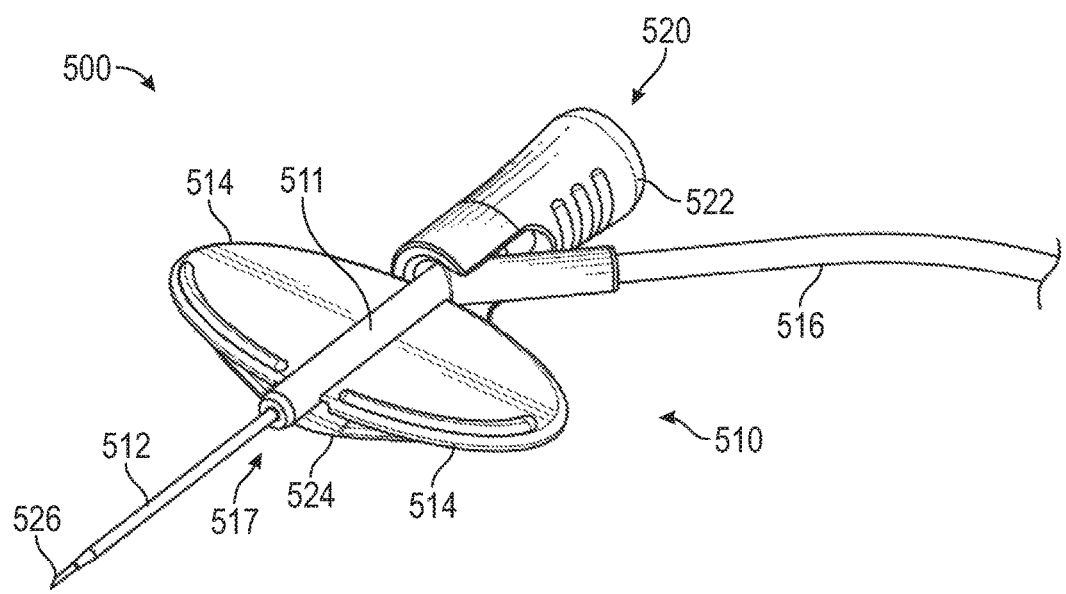
FIG. 6B is an isometric top view of a catheter system including the catheter adapter of FIG. 6A and a needle component fully inserted into the catheter adapter.

FIGS. 4A-5 illustrate various views of a catheter system 400, according to another embodiment of the present disclosure. FIGS. 4A-4C show the catheter system 400 with a needle component 420 in various positions relative to a compliant catheter adapter 410 and FIG. 5 shows a cross-sectional view of the catheter system 400 of FIG. 4B. The catheter system 400 may include similar features to other catheter system described herein, such as: a catheter adapter body 411 having a proximal end 415 and a distal end 417, a catheter lumen 412, a compression cap 413, one or more stabilization members 414, an extension tube 416, an inner chamber 440, a port 470, a catheter wedge 480, a needle hub 422, a grip 424, and a needle 426. Furthermore, as can be seen in FIG. 5, the catheter system 400 may also include a first compression resistant septum 451, a second compression resistant septum 452, a septum chamber 456 intermediate the first compression resistant septum 451 and the second compression resistant septum 452, a first lumen 457, and a second lumen 458.

The first compression resistant septum 451 may be positioned to abut at least a portion of the proximal end 415 of the catheter adapter body 411 and/or the second compression resistant septum 452. The first lumen 457 may be configured to receive an elongate object. The second compression resistant septum 452 may include a second lumen 458 formed there through which may also be configured to receive the elongate object. In at least some embodiments, the second compression resistant septum 452 may be disposed within the inner chamber 440 of the catheter adapter body 411. The second compression resistant septum 452 may be positioned to abut the first compression resistant septum 451 and the septum chamber 456 may be formed between the first compression resistant septum 451 and the second compression resistant septum 452. The compression cap 413 may be configured to couple the first compression resistant septum 451 to the catheter adapter body 411 and/or the second compression resistant septum 452. The compression cap 413 and/or the catheter adapter body 411 may be configured to impart a radial compression force to the first compression resistant septum 451 and/or the second compression resistant septum 452 such that the first lumen 457 and/or the second lumen 458 narrow and seal when the elongate object is removed from the first lumen 457 and/or the second lumen 458. In at least one embodiment, the compression cap 413, the first compression resistant septum 451, and/or the second compression resistant septum 452 may be positioned within the proximal end 415 of the catheter adapter body 411, as shown in FIG. 5.

In at least one embodiment, one of the first septum 451 and the second septum 452 may be pressure capable and compression resistant, while the other of the first septum 451 and the second septum 452 may not necessarily be pressure capable and compression resistant. For example, the first septum 451 may not be pressure capable and compression resistant while the second septum 452 may be pressure capable and compression resistant, and vice versa.

Figure 7A:
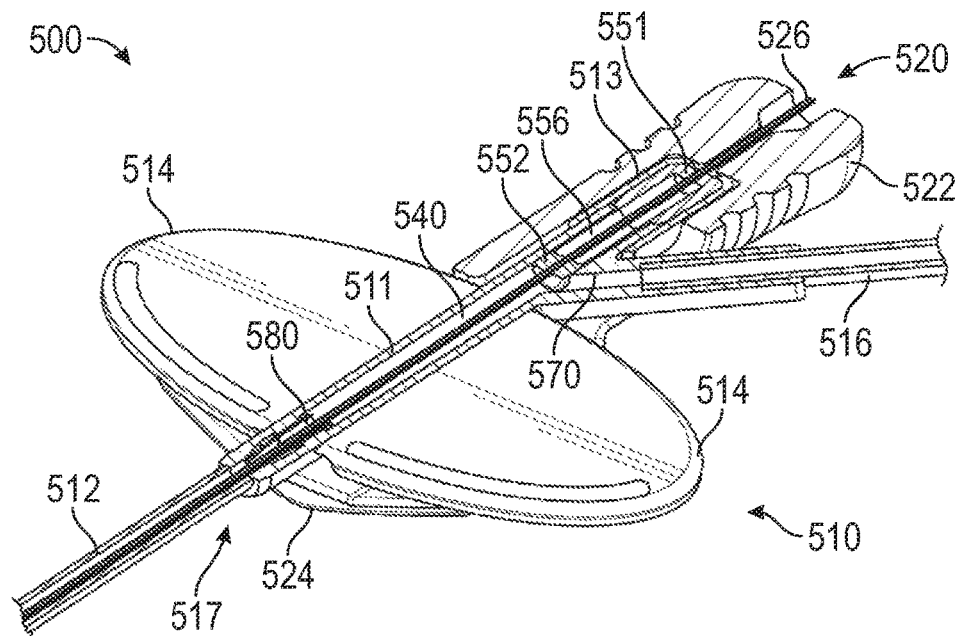
FIG. 7A is a cross-sectional isometric view of the catheter system of FIG. 6B.
Figure 7B:
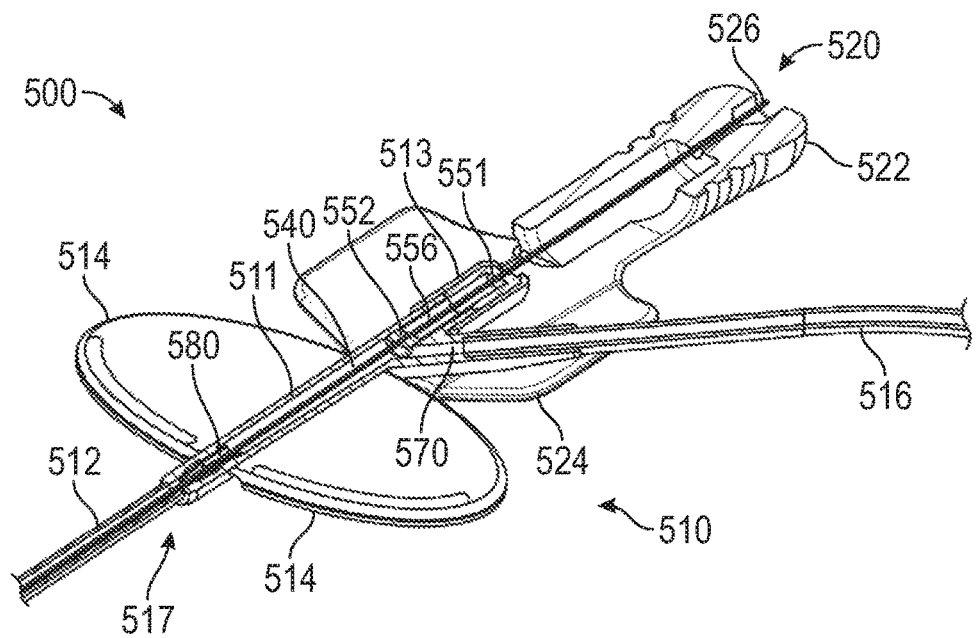
FIG. 7B is a cross-sectional isometric view of the catheter system of FIG. 6B with the needle component partially removed from the catheter adapter.
Figure 8:
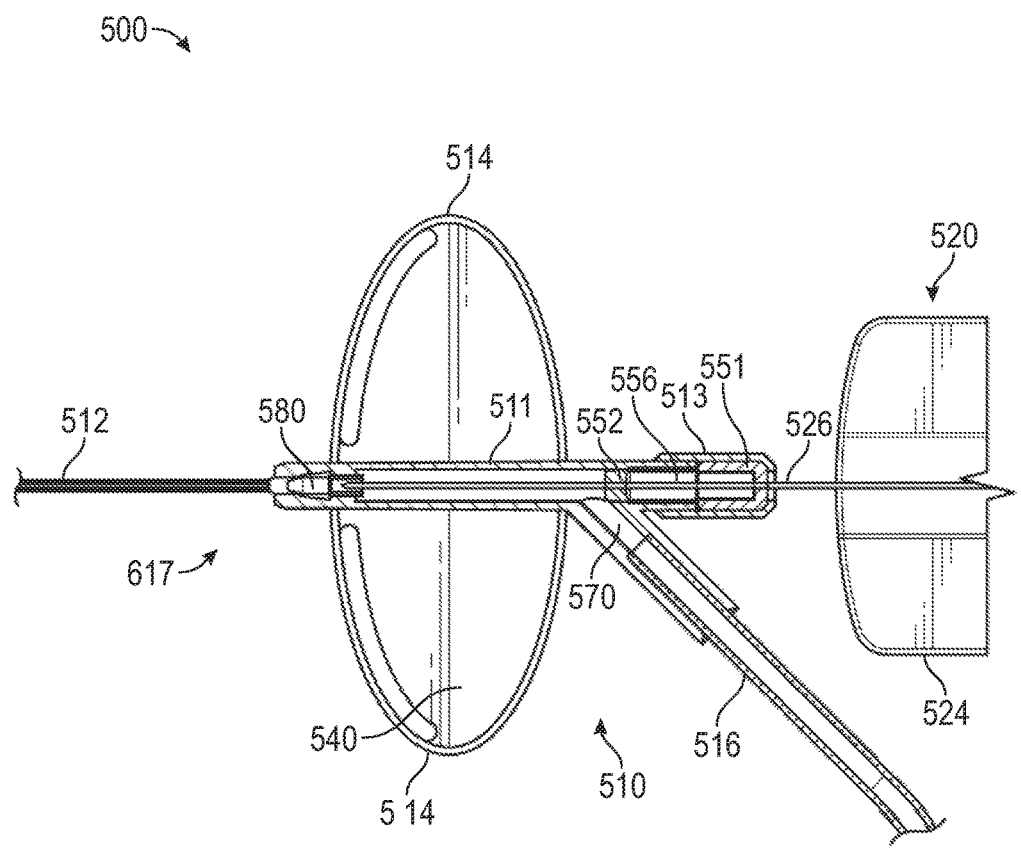
FIG. 8 is a cross-sectional top view the catheter system of FIG. 6B with the needle component partially removed from the catheter adapter.

FIGS. 6A-8 illustrate various views of a catheter system 500, according to another embodiment of the present disclosure. The catheter system 500 may include similar features to other catheter system described herein, such as: a catheter adapter body 511 having a proximal end 515 and a distal end 517, a catheter lumen 512, a compression cap 513, one or more stabilization members 514, an extension tube 516, an inner chamber 540, a port 570, a catheter wedge 580, a needle hub 522, a grip 524, and a needle 526. Furthermore, as can be seen in FIGS. 7A-8, the catheter system 500 may also include a first compression resistant septum 551 with a first lumen formed there through, a second compression resistant septum 552 with a second lumen formed there through, and a septum chamber 556 intermediate the first compression resistant septum 551 and the second compression resistant septum 552.

The first compression resistant septum 551 may be positioned to abut at least a portion of the proximal end 515 of the catheter adapter body 511 and/or the second compression resistant septum 552. The first and second lumens may be configured to receive an elongate object. In at least some embodiments, the second compression resistant septum 552 may be disposed within the inner chamber 540 of the catheter adapter body 511. The second compression resistant septum 552 may be positioned to abut the first compression resistant septum 551 and the septum chamber 556 may be formed between the first compression resistant septum 551 and the second compression resistant septum 552. The compression cap 513 may be configured to couple the first compression resistant septum 551 to the catheter adapter body 511 and/or the second compression resistant septum 552. The compression cap 513 may also be configured to impart a radial compression force to the first compression resistant septum 551 and/or the second compression resistant septum 552 such that the first lumen and the second lumen narrow and seal when the elongate object is removed from the first lumen and the second lumen.

Figure 9A:
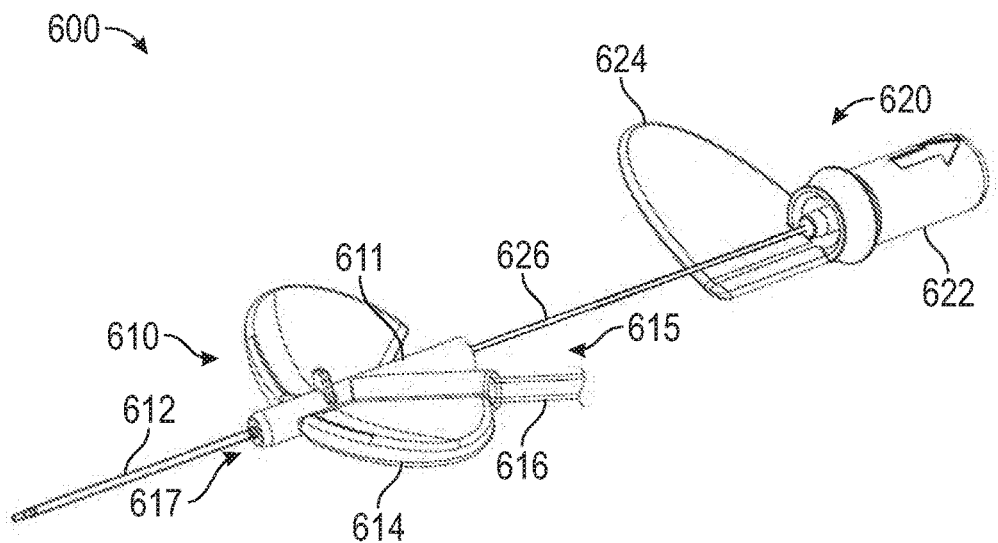
FIG. 9A is an isometric view of a catheter system with a needle component removed from a catheter adapter, according to another embodiment of the present disclosure.
Figure 9B:
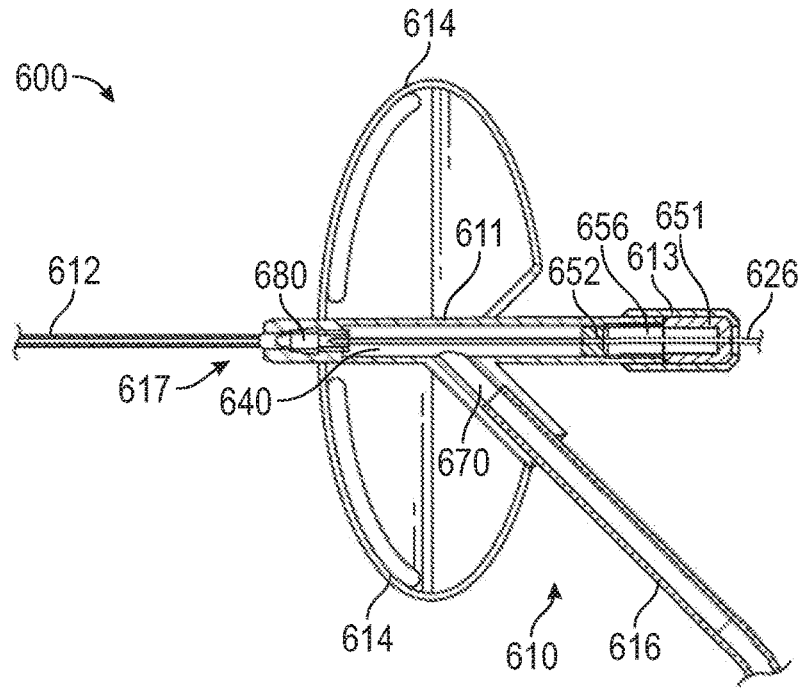
FIG. 9B is a cross-sectional top view of the catheter system of FIG. 9A.

FIGS. 9A and 9B illustrate two views of a catheter system 600, according to another embodiment of the present disclosure. The catheter system 600 may include similar features to other catheter system described herein, such as: a compliant catheter adapter 610 including a catheter adapter body 611 having a proximal end 615 and a distal end 617, a catheter lumen 612, a compression cap 613, one or more one or more stabilization members 614, an extension tube 616, an inner chamber 640, a port 670, and a catheter wedge 680. The catheter system 600 may also have a needle component 620 including a needle hub 622, a grip 624, and a needle 626. Furthermore, as can be seen in FIGS. 9A and 9B, the catheter system 600 may also include a first compression resistant septum 651 with a first lumen formed there through, a second compression resistant septum 652 with a second lumen formed there through, and a septum chamber 656 intermediate the first compression resistant septum 651 and the second compression resistant septum 652.

The first compression resistant septum 651 may be positioned to abut at least a portion of the proximal end 615 of the catheter adapter body 611 and/or the second compression resistant septum 652. The first and second lumens may be configured to receive an elongate object. In at least some embodiments, the second compression resistant septum 652 may be disposed within the inner chamber 640 of the catheter adapter body 611. The second compression resistant septum 652 may be positioned to abut the first compression resistant septum 651 and the septum chamber 656 may be formed between the first compression resistant septum 651 and the second compression resistant septum 652. The compression cap 613 may be configured to couple the first compression resistant septum 651 to the catheter adapter body 611 and/or the second compression resistant septum 652. The compression cap 613 may also be configured to impart a radial compression force to the first compression resistant septum 651 and/or the second compression resistant septum 652 such that the first lumen and the second lumen narrow and seal when the elongate object is removed from the first lumen and the second lumen.

FIGS. 10A-F show various isometric side views of the proximal ends of differently shaped needles, according to embodiments of the present disclosure. The proximal ends of the differently shaped needles shown in FIGS. 10A-F may help facilitate the assembly process of catheter systems of the present disclosure via a "self-slitting" process. For example, prior needle designs typically have distal ends with sharp bevel tips to facilitate penetration of a patients' skin and blood vessels as well as blunt shaped proximal ends that may be coupled to a suitable needle hub during assembly of the catheter system. However, blunt shaped proximal ends typically require that a lumen or slit first be formed in the septum via a "pre-slitting" process in order to allow passage of the proximal end of the needle through the septum for coupling to a suitable needle hub. This "pre-slitting" process increases manufacturing efforts and costs. Furthermore, any off-slit landing of the proximal end of the needle on the septum during assembly may result in: (1) coring out a piece of septum material; (2) unduly stretching and/or extending the septum slit (i.e., lumen) in an extreme fashion; and/or (3) entirely missing the slit, creating another passage or hole through the septum. All of the foregoing scenarios may lead to significant undesirable fluid leakage.

Additionally, prior needle designs may suffer difficulties during the bonding process of the proximal end of the needle to a suitable needle hub. For example, press fitting a blunt shaped needle proximal end into a needle hub via an interference fit may result in "skiving" the interference fit region of the hub, as will be discussed in more detail below with reference to FIG. 12B. Moreover, crimping and/or gluing the needle proximal end into a needle hub may seal off the cannula of the needle and disable extended blood "flashback" capabilities which may be desirable for continuous vein confirmation (i.e., visualization of blood flowing out of the cannula of the needle as the needle is advanced into the patient's vein).

Furthermore, features on a needle that enable visualization of flashback at different stages of catheter insertion may be desirable. For example, needle features (such as a second proximal notch) may enable both instantaneous and extended/secondary flashback in comparison to a simple open lumen notch design with a single notch at the distal end of the needle and a sealed proximal end preventing extended/secondary flashback. Typical needle designs that allow visualization of instantaneous flashback (i.e., "Insta-Flash") may include a passage near the insertion end of the needle through the cannula wall to allow blood to enter the space between the needle and the catheter tubing, however addition of a secondary notch may also allow for crimping and/or gluing of the proximal end of the needle to a suitable needle hub without obstructing the fluid path for extended/secondary flashback.

The needles disclosed in FIGS. 10A-13F may overcome the above challenges by: (1) allowing the needle to slit the septum directly during assembly to avoid the pre-slitting process; (2) creating a custom-shaped lumen in the septum without damaging the septum; (3) allowing the needle to penetrate the septum without being deflected off center; (4) facilitating advancement through a glue well or press-fit channel formed in a suitable needle hub by providing a "lead-in" shape that reduces risk of damage during assembly caused by slight misalignments; (5) reducing the risk of the needle stalling at the interior of the septum or needle hub during assembly; (6) varying the shape of the proximal end of the needle may create different shaped slits or lumens through the septum which may be optimized to help reduce drag force as the needle is drawn through the septum; and (7) providing additional notches to improve flashback processes.

Figure 10A:
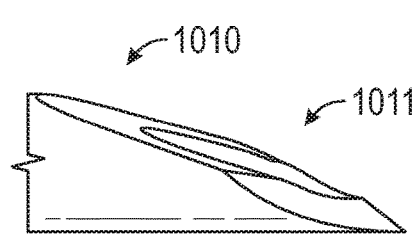
FIGS. 10A-F show isometric side views of the proximal ends of differently shaped needles.
Figure 10B:
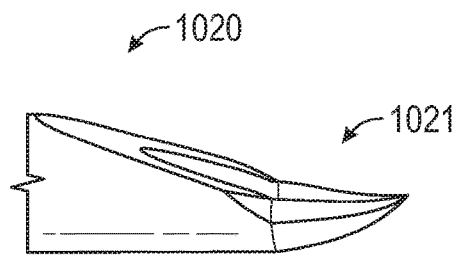
Figure 10C:
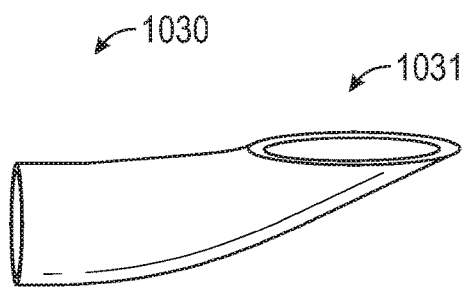
Figure 10D:
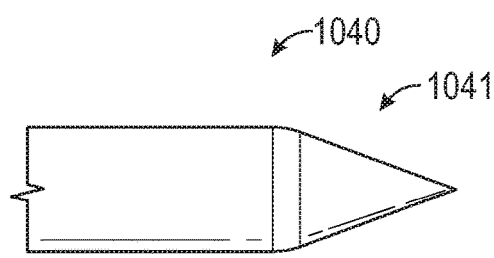
Figure 10E:
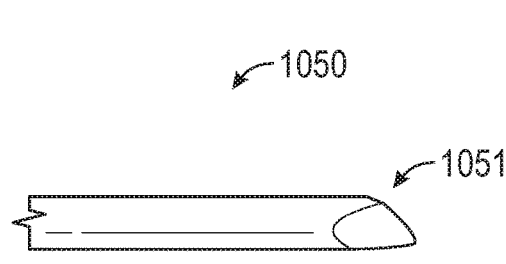
Figure 10F:
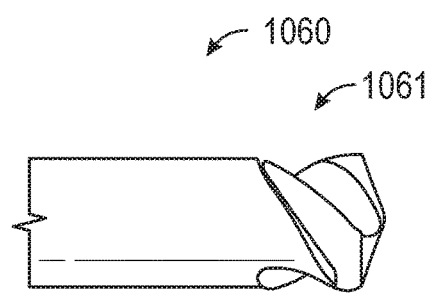

FIG. 10A shows an isometric side view of a proximal end 1010 of a needle that includes a beveled surface 1011 configured to form a lumen (or slit) through a septum as the proximal end 1010 of the needle is urged through a septum. The beveled surface 1011 may be formed via any suitable process known in the art, such as a grounding process. FIG. 10B shows an isometric side view of a proximal end 1020 of a needle that includes a "rolled" beveled surface 1021 configured to form a lumen through a septum as the proximal end 1020 of the needle is urged through a septum. The "rolled" beveled surface 1021 can be formed via a grounding process combined with a rolling process to form a sharp point toward the center of the needle. FIG. 10C shows an isometric side view of a proximal end 1030 of a needle that includes a "rolled" and "flattened" beveled surface 1031 configured to form a lumen through a septum as the proximal end 1030 of the needle is urged through a septum. The "rolled" and "flattened" beveled surface 1031 can be formed via a grounding process combined with a rolling process and a flattening process. This shape can help eliminate angled deflection during insertion of the proximal end 1030 of the needle through a septum. FIG. 10D shows an isometric side view of a proximal end 1040 of a needle that includes a conically-pointed surface 1041 configured to form a lumen through a septum as the proximal end 1040 of the needle is urged through a septum. The conically-pointed surface 1041 can be formed via any suitable process known in the art. FIG. 10E shows an isometric side view of a proximal end 1050 of a needle that includes a blade-shaped surface 1051 configured to form a lumen through a septum as the proximal end 1050 of the needle is urged through a septum. The blade-shaped surface 1051 can be formed via any suitable process known in the art. FIG. 10E shows an isometric side view of a proximal end 1050 of a needle that includes a blade-shaped surface 1051 configured to form a lumen through a septum as the proximal end 1050 of the needle is urged through a septum. The blade-shaped surface 1051 can be formed via any suitable process known in the art. FIG. 10F shows an isometric side view of a proximal end 1060 of a needle that includes a spiral-cut shaped surface 1061 configured to form a lumen through a septum as the proximal end 1060 of the needle is urged through a septum. The spiral-cut shaped surface 1061 may be formed via any suitable process known in the art.

Figure 11A:
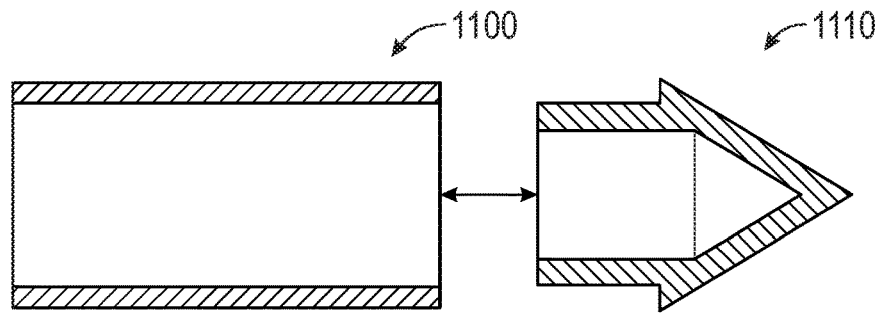
FIGS. 11A-C show isometric cross-sectional side views of the proximal end of a needle with a separable tip, according to another embodiment of the present disclosure.
Figure 11B:
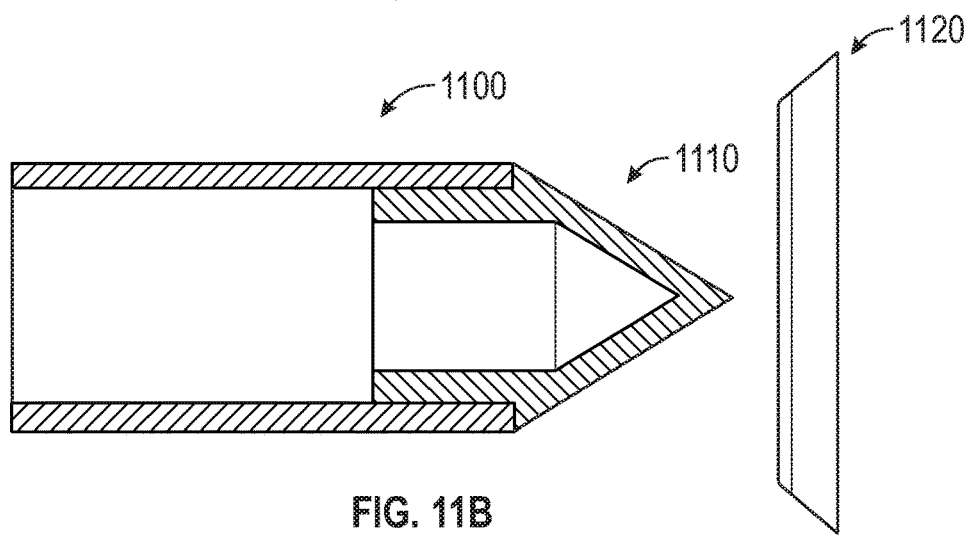
Figure 11C:
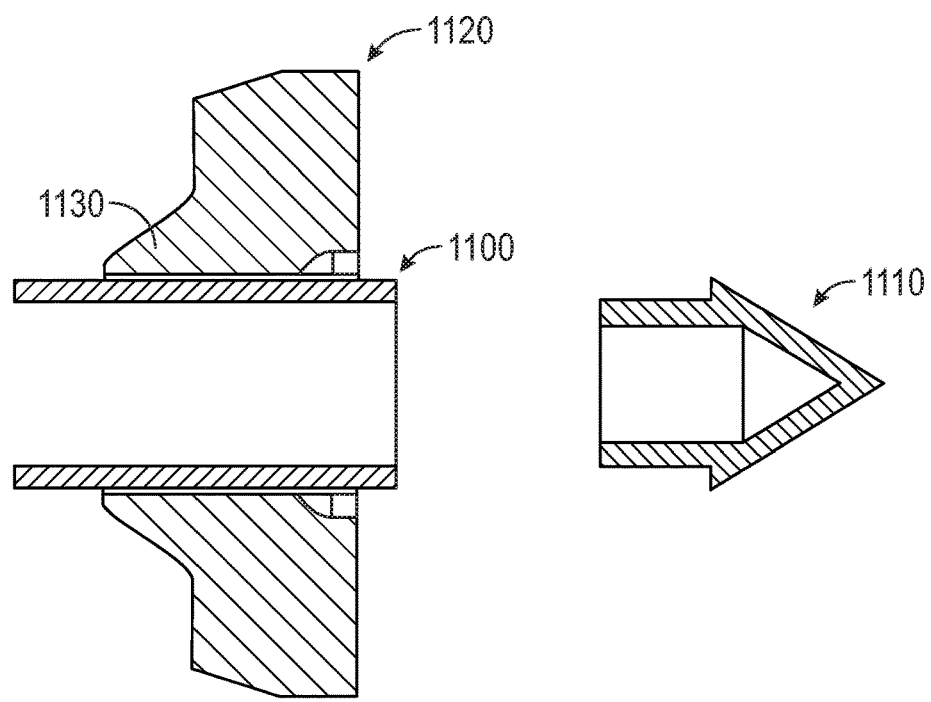

FIGS. 11A-11C illustrate various isometric cross-sectional side views of a proximal end 1100 of a needle with a separable tip 1110, according to another embodiment of the present disclosure. In this embodiment, the proximal end 1100 of the needle may be blunt and/or hollow such that a suitably shaped separable tip 1110 may be coupled to the proximal end 1100 of the needle, as shown in FIGS. 11A and 11B. The assembled proximal end 1100 of the needle and separable tip 1110 may then be urged against a septum 1120 as shown in FIG. 11B to penetrate the septum 1120 and form a lumen 1130 there through. Once proximal end 1100 of the needle and separable tip 1110 pass through the septum, the separable tip 1110 may then be decoupled and removed from the proximal end 1100 of the needle and the proximal end 1100 of the needle may be further coupled to a suitable needle hub. In at least one embodiment, the separable tip 1110 may be batch fabricated (e.g. by injection molding processes) and/or may be reusable. The separable tip 1110 may also be removed from the proximal end 1100 of a needle by any suitable process (e.g., via compressed air, mechanical removal, via a dissolving solution, etc.).

Figure 12A:
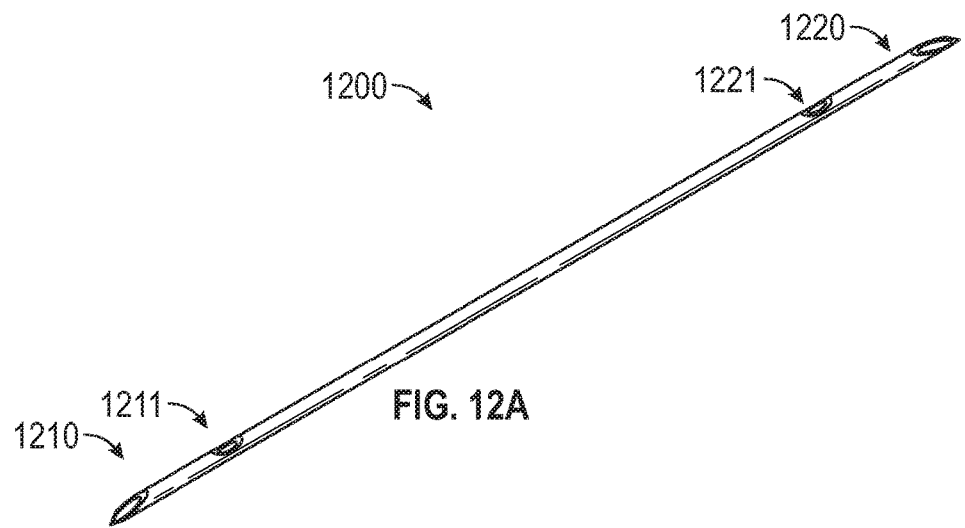
FIG. 12A shows an isometric view of a needle with notches formed therein.
Figure 12B:
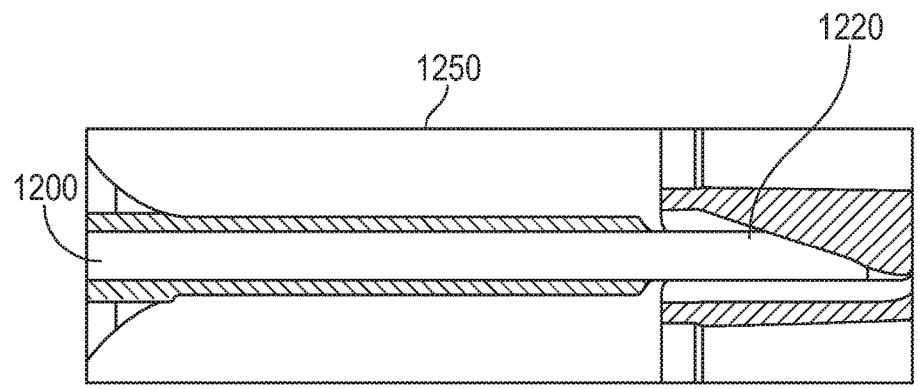
FIG. 12B shows a cross-sectional side view of the needle of FIG. 12A inserted into a needle hub.

FIG. 12A shows an isometric view of an example needle 1200 with a distal 1210 end having a distal notch 1211 formed therein, as well as a proximal 1220 end having a proximal notch 1221 formed therein, forming an open lumen at the distal 1210 end and at the proximal 1220 end of the needle to help visualize flashback at selected spots of the needle, as previously discussed. FIG. 12B also shows a cross-sectional side view of the proximal end 1220 of the needle 1200 of FIG. 12A inserted into a needle hub 1250. As previously discussed, the needle 1200 may be held in place by any suitable method, including but not limited to: a press fit or compression fit mechanism, adhesives, a crimping force, a bend formed in the needle, etc.

Figure 13A:
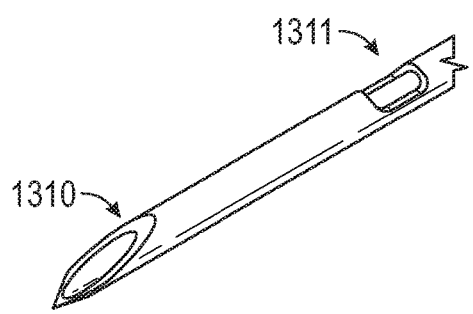
FIGS. 13A-F show isometric views of the distal ends of various needles with differently shaped notches formed therein.
Figure 13B:
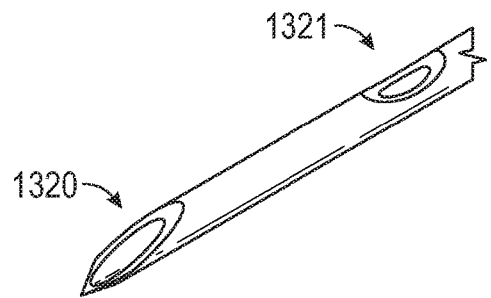
Figure 13C:
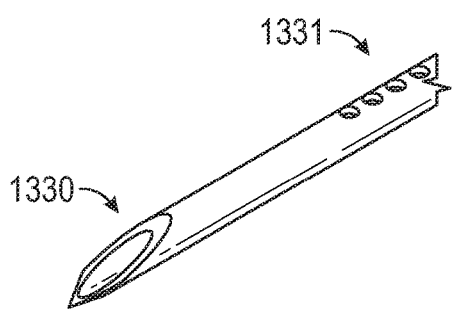
Figure 13D:
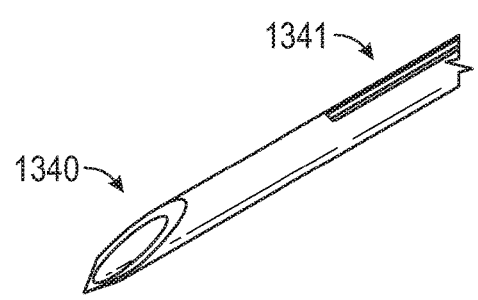
Figure 13E:
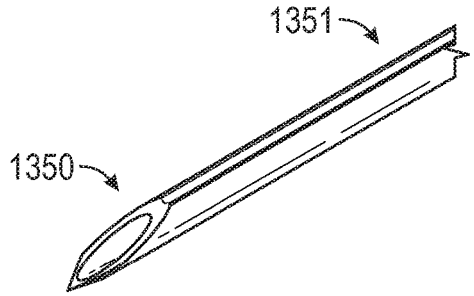
Figure 13F:
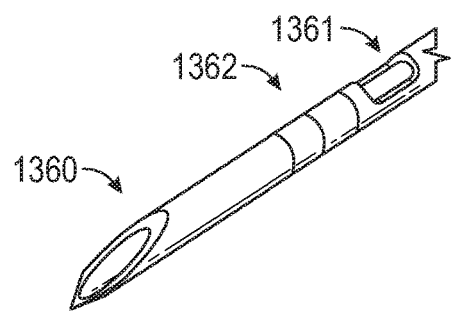

FIGS. 13A-F show isometric views of the distal ends of various non-limiting examples of needles having different notch designs formed therein. FIG. 13A shows an isometric side view of a proximal end 1310 of a needle with a straight cut-shaped notch 1311 formed therein. FIG. 13B shows an isometric side view of a proximal end 1320 of a needle with a scalloped-shaped notch 1211 formed therein for smooth needle movement through the septum during assembly and catheter advancement. FIG. 13C shows an isometric side view of a proximal end 1330 of a needle with one or more small holes 1231 formed therein. FIG. 13D shows an isometric side view of a proximal end 1340 of a needle with a slot-shaped notch 1341 formed therein. FIG. 13E shows an isometric side view of a proximal end 1350 of a needle with an axial groove 1351 formed therein. FIG. 13F shows an isometric side view of a proximal end 1360 of a needle with a straight cut-shaped notch 1361 formed therein and a raised bump 1362 which may enable a safety mechanism, as will be discussed on more detail below with reference to FIG. 15. Each of the above notch designs may help enable varying capabilities of flashback, as discussed previously. Moreover, each notch design may help achieve a desired mechanical strength at the area of the notch depending on the size and shape of the notch or notches chosen.

Figure 14A:
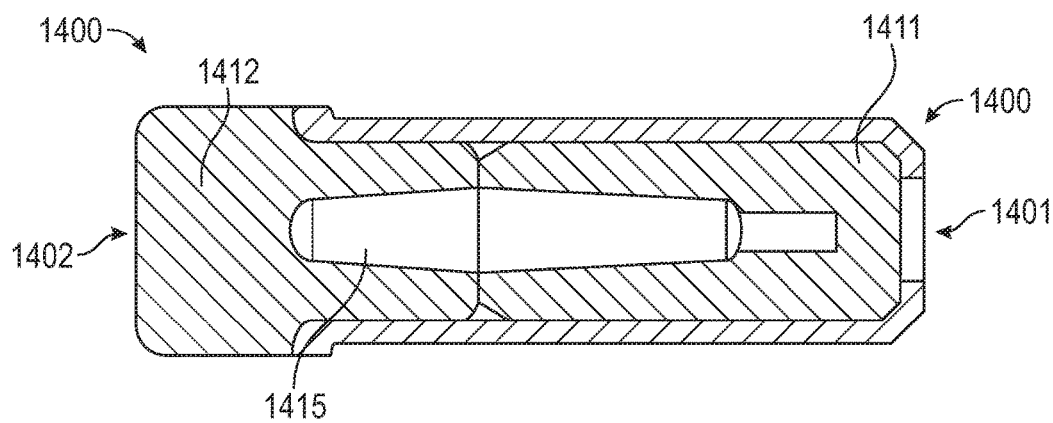
FIG. 14A shows a cross-sectional side view of a septum assembly, according to an embodiment of the present disclosure.
Figure 14B:
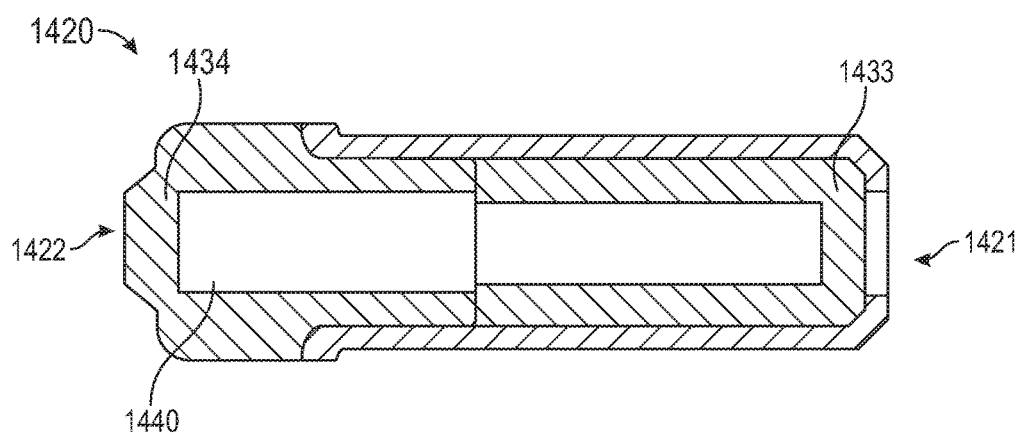
FIG. 14B shows a cross-sectional side view of a septum assembly, according to another embodiment of the present disclosure.

FIG. 14A shows a cross-sectional side view of an example septum assembly 1400. The septum assembly 1400 may include a proximal end 1401, a distal end 1402, a first septum 1411 having a first thickness, a second septum 1412 having a second thickness, and a septum chamber 1415. FIG. 14B shows a cross-sectional side view of another example septum assembly 1420. The septum assembly 1420 may also include a proximal end 1421, a distal end 1422, a third septum 1433 having a third thickness, a fourth septum 1434 having a fourth thickness, and a septum chamber 1440. The force required to draw a needle through the septa 1400, 1420 may vary depending on the different thicknesses of the various septa 1411, 1412, 1433, 1434. For example, the greater a thickness of the septa 1411, 1412, 1433, 1434 becomes, the more frictional force a needle may experience as it moves through the septa, and hence the more drag force or resistance force the needle may experience. Conversely, less thick septa 1411, 1412, 1433, 1434, may impart less frictional force on a needle as it moves through the septa 1411, 1412, 1433, 1434, and hence the drag force or resistance force on the needle may be less. As can be seen in FIG. 14B, the septa 1433, 1434 of FIG. 14B are thinner than the septa 1411, 1412 of FIG. 14A. Thus, a needle passing through the septum assembly of FIG. 14B, in general, should experience less drag force or resistance given the same material for each septum assembly 1400, 1420.

Figure 14C:
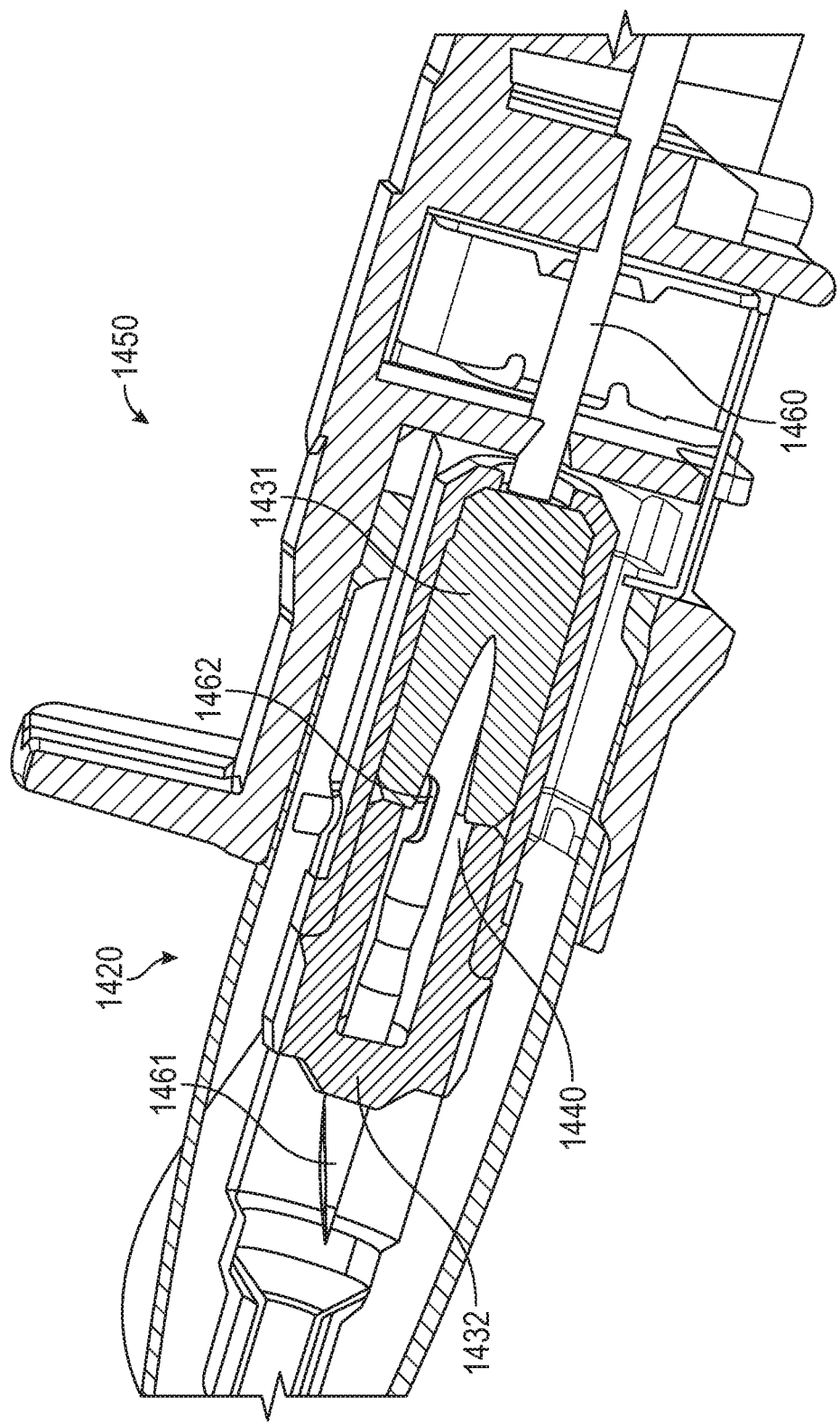
FIG. 14C shows an isometric cross-sectional side view of the septum assembly of FIG. 14B within a catheter system with the distal tip of a needle disposed within the septum assembly.

FIG. 14C shows an isometric cross-sectional side view of the septum assembly 1420 of FIG. 14B housed within a catheter system 1450 with a distal end 1461 of a needle 1460 disposed through the septum assembly 1420 and a notch 1462 formed in the needle 1460 that is disposed within the septum chamber 1440. In the embodiment shown in FIG. 14C, an axial length of the septum chamber 1440 may be chosen to be sufficiently long to simultaneously enclose both the distal tip 1461 of the needle 1460 and the notch 1462 therein to preclude fluids from bypassing the septum 1420 through the notch 1462 should the notch become exposed beyond the proximal end 1421 of the septum assembly 1420.

Figure 15:
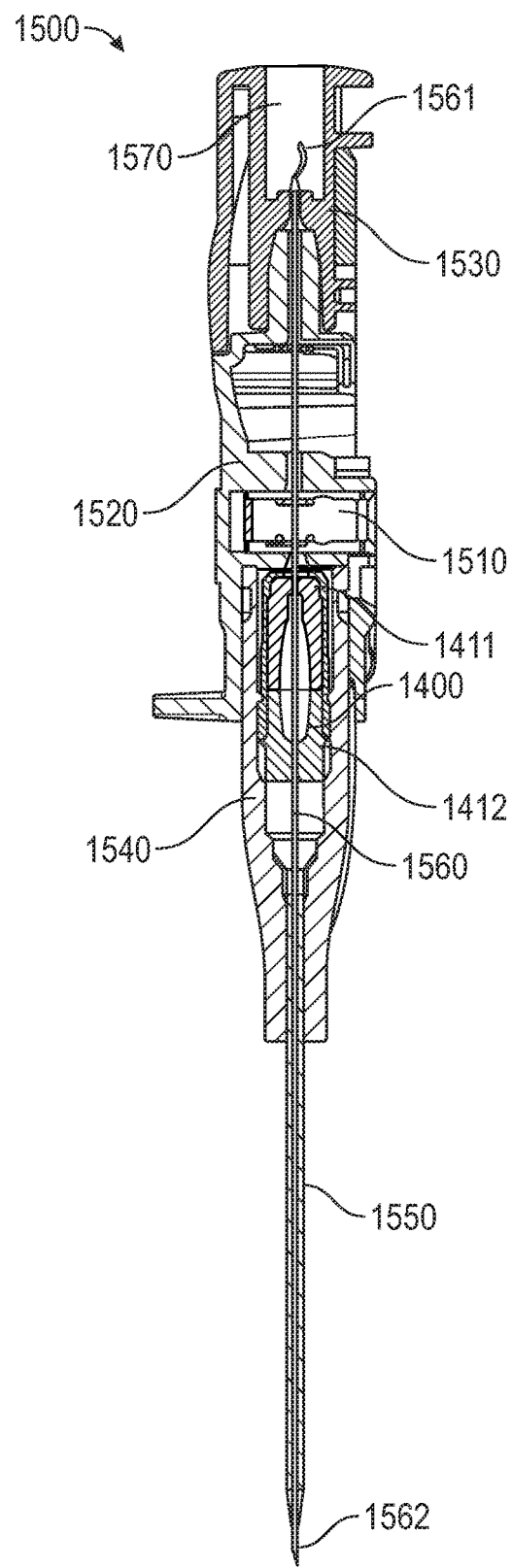
FIG. 15 shows an isometric cross-sectional side view of the septum assembly of FIG. 14A within an assembled catheter system.

FIG. 15 shows an isometric cross-sectional side view of the septum assembly 1400 of FIG. 14A housed within a catheter system 1500. The catheter system 1500 may include a needle 1560 (shown fully inserted inside the catheter system 1500) with a proximal end 1561 coupled to a needle hub 1570 (by an suitable means as previously discussed) as well as a distal end 1562 shown protruding beyond the catheter 1550. The catheter system 1500 may also include a safety mechanism composed of various parts including, but not limited to: a V-clip 1510 (or spring), a tip shield 1520, a retaining washer (not shown), and a grip 1530. The tip shield 1520 may be rigid and/or configured to encase the distal end 1562 of the needle 1560 when the distal end 1562 of the needle 1560 is extracted from the catheter 1550 after a vein has been accessed. In at least one embodiment, the V-clip 1510 may be coated with a material (such as paralyne) which enhances the performance/feel of the needle 1560 rubbing against the V-clip 1510 as it is drawn through the V-clip 1510. The V-clip 1510 may secure the tip shield 1520 to the catheter adapter 1540 until the needle 1560 is removed from the catheter 1550, at which point the V-clip 1510 may be activated and release the tip shield 1520 from the catheter adapter 1540 to block the path for the needle 1560 through a distal end of the tip shield 1520 and ensuring the distal end 1562 of the needle 1560 does not become re-exposed. The retaining washer may be inserted in a proximal end of the tip shield 1520 to bind to the needle 1560 at a deformation or raised bump (not shown) formed on the needle 1560 and located on the distal end 1562 of the needle 1560 in order to prevent extraction of the distal end 1562 of the needle 1560 from the tip shield 1520. Moreover, the grip 1530 may secure the needle 1560 in place axially and facilitate removal of the needle 1560 after the catheter 1550 has been placed in the vasculature.

It will be noted that in some embodiments a particular catheter device, such as, for example, any of the catheter devices of FIGS. 1A-15 may also include a needle safety mechanism. The safety mechanism may include any safety mechanism configured to secure a sharpened, distal tip of an introducer needle when the needle is withdrawn from a catheter of the particular catheter device, preventing accidental needle sticks.

The safety mechanism may be coupled with the particular catheter device in any number of ways. In some embodiments, the safety mechanism may include an internal interlock in which the safety mechanism is coupled with an internal surface of a catheter adapter. Coupling may include threading, fitting, snapping, connecting, attaching, fastening, clipping, hooking, or any other suitable means of coupling. Non-limiting examples of safety mechanisms that include an internal interlock are provided in: U.S. Pat. No. 8,496,623, titled BI-DIRECTIONAL CANNULA FEATURE CAPTURE MECHANISM, filed Mar. 2, 2009; U.S. Pat. No. 9,399,120, titled BI-DIRECTIONAL CANNULA FEATURE CAPTURE MECHANISM, filed Jul. 11, 2013; U.S. Patent Application No. 62/314,262, titled CANNULA CAPTURE MECHANISM, filed Mar. 28, 2016, each of which is herein incorporated by reference in its entirety. In some embodiments, the safety mechanism may include a clip disposed within the catheter adapter, a non-limiting example of which is provided in U.S. Pat. No. 6,117,108, titled SPRING CLIP SAFETY IV CATHETER, filed Jun. 12, 1998, which is herein incorporated by reference in its entirety.

In some embodiments, the safety mechanism may include an external interlock in which the safety mechanism is coupled with an external surface of the catheter adapter. In some embodiments, the safety mechanism may be coupled with an external surface of the catheter adapter and an internal and/or external surface of a needle hub. Coupling may include threading, fitting, snapping, connecting, attaching, fastening, clipping, hooking, or any other suitable means of coupling. Non-limiting examples of safety mechanisms that include an external interlock are provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. In some embodiments, the safety mechanism may include a V-clip or a similar clip. A non-limiting example of a V-clip is provided in U.S. patent application Ser. No. 14/295,953, titled PORTED IV CATHETER HAVING EXTERNAL NEEDLE SHIELD AND INTERNAL BLOOD CONTROL SEPTUM, filed Jun. 4, 2014, which is herein incorporated by reference in its entirety. The V-clip may selectively retain a portion of the catheter adapter.

In some embodiments, a defeatable mechanical connection is provided between the safety mechanism and at least one other component of the IV catheter system. In some instances, the mechanical connection is defeated upon securement of the distal tip of the needle within the safety mechanism. In some embodiments, a surface of the safety mechanism is selectively coupled to one or more of the following: the catheter adapter, a blood control valve, an extension tube, and one or more paddle grips.

In some embodiments, the safety mechanism may include a safety barrel, which may be spring-loaded. For example, the safety barrel may be spring loaded as in the BD™ Insyte® Autoguard™ BC shielded protective IV catheter. In some embodiments, the safety mechanism may be passively and/or actively activated. In some embodiments, the safety mechanism may be configured to interact with a needle feature, such as a ferrule, notch, crimp or bump on the needle. In some embodiments, the safety mechanism may include an arm or lever that may be actuated to capture the distal tip within the safety mechanism and prevent the tip from emerging prior to safe disposal. In some embodiments, the safety mechanism may be attached to a body of the needle and may be capable of sliding along the length thereof.

In some embodiments, in an assembled position prior to catheterization, the safety mechanism may be disposed between the catheter adapter and the needle hub. In some embodiments, the catheter adapter and the needle hub may be spaced apart by at least a portion of the safety mechanism in the assembled position prior to catheterization. In some embodiments, in the assembled position prior to catheterization, a proximal end of the catheter adapter may be disposed between a distal end of the safety mechanism and a distal end of a grip of the needle hub, such as, for example, a paddle grip. In some embodiments, in the assembled position prior to catheterization, the proximal end of the catheter adapter body may be disposed between the distal end of the safety mechanism and a proximal end of the grip of the needle hub. In some embodiments, a portion of the safety mechanism may overlap with a portion of the grip of the needle hub. In some embodiments, at least a portion of at least one of the catheter adapter and the grip overlaps at least some portion of the safety mechanism. In some embodiments, no portion of the catheter adapter body or the grip overlaps any portion of the safety mechanism.

In at least some embodiments, the distal end 1562 of the needle 1560 may be threaded through the various components of the catheter system 1500 described above and shown in FIG. 15. Any of the needle geometries shown in FIGS. 10A-13F may also be utilized by the distal end 1562 of the needle 1560 to provide an advantageous lead-in geometry to facilitate assembly of the distal end 1562 of the needle 1560 through the various components of the catheter system 1500, thus avoiding damage to the components of the catheter system 1500 and/or damage to the needle 1560 itself.

The present disclosure may be embodied in other specific forms without departing from its structures, methods, or other essential characteristics as broadly described herein and claimed hereinafter. The described embodiments are to be considered in all respects only as illustrative, and not restrictive. The scope of the present disclosure is, therefore, indicated by the appended claims, rather than by the foregoing description. All changes that come within the meaning and range of equivalency of the claims are to be embraced within their scope.

What is claimed is:

1. A compliant catheter adapter comprising:
   a needle comprising:
      a proximal end, the proximal end of the needle shaped to facilitate a self-slitting/self-guiding process during assembly of the catheter adapter;
      a distal end; and
      a plurality of openings disposed along the needle between the proximal end and the distal end of the needle, wherein the plurality of openings are configured to facilitate flashback visualization;
   a catheter adapter body formed of a compliant material, the catheter adapter body comprising:
      a proximal end and a distal end, the catheter adapter body having a generally elongate shape formed about a longitudinal axis extending between the proximal end and the distal end of the catheter adapter body;
      an inner chamber disposed within the catheter adapter body, the inner chamber having a generally elongate shape formed about the longitudinal axis extending between the proximal end and the distal end of the catheter adapter body;
      a compression resistant septum comprising a distal end formed in the compliant material of the catheter adapter body, the compression resistant septum further comprising a proximal end, wherein the distal end of the compression resistant septum and the catheter adapter body are integrally formed of the same compliant material, the compression resistant septum disposed toward the proximal end of the catheter adapter body; and
      a lumen formed through the compression resistant septum by the proximal end of the needle during the self-slitting process as the catheter adapter is assembled; and
   a compression cap coupled to the proximal end of the compression resistant septum, the compression cap configured to impart a radial compression force to the compression resistant septum such that the lumen narrows and seals when the needle is removed from the lumen.

2. The compliant catheter adapter of claim 1, wherein the catheter adapter body is integrally formed from a compression set resistant elastomeric material.

3. The compliant catheter adapter of claim 2, wherein the compression set resistant elastomeric material comprises one of a thermoplastic elastomer material, a liquid silicone rubber material, and a polyisoprene material.

4. The compliant catheter adapter of claim 1, wherein the compression cap further comprises:
   a proximal end having a first aperture configured to receive the needle there through;
   a distal end having a second aperture configured to receive at least a portion of the catheter adapter body; and
   a compression surface extending intermediate the proximal end and the distal end of the compression cap, the compression surface enclosing a hollow portion formed in the compression cap, the hollow portion configured to receive at least a portion of the compression resistant septum therein, and the compression surface configured to impart the radial compression force to the compression resistant septum such that the lumen narrows and seals when the needle is removed from the lumen.

5. The compliant catheter adapter of claim 4, wherein the compression cap is a separate piece that is coupled to the compression resistant septum.

6. The compliant catheter adapter of claim 4, wherein the compression cap is integrally formed with the compression resistant septum.

7. The compliant catheter adapter of claim 6, wherein the compression cap is coupled to the compression resistant septum through an over-molding manufacturing process.

8. The compliant catheter adapter of claim 1, further comprising:
   one or more stabilization members coupled to the catheter adapter body and configured to stabilize the catheter adapter body with respect to a patient;
   a port in fluid communication with the inner chamber and configured to receive an extension tube, the port comprising one of a Y-shaped port, a T-shaped port, a V-shaped port and a parallel-shaped port;
   a catheter lumen coupled to and extending from the distal end of the catheter adapter body; and
   a catheter wedge disposed toward the distal end of the catheter adapter body and configured to guide the needle into the catheter lumen as the needle is inserted through the catheter adapter body.

9. A compliant catheter adapter comprising:
   a needle comprising:

a proximal end, the proximal end of the needle shaped to facilitate a self-slitting/self-guiding process during assembly of the catheter adapter;
a distal end; and
a plurality of openings disposed along the needle between the proximal end and the distal end of the needle, wherein the plurality of openings are configured to facilitate flashback visualization;
a catheter adapter body formed of a compliant material, the catheter adapter body comprising:
a proximal end and a distal end, the catheter adapter body having a generally elongate shape formed about a longitudinal axis extending between the proximal end and the distal end of the catheter adapter body; and
an inner chamber disposed within the catheter adapter body, the inner chamber having a generally elongate shape formed about the longitudinal axis extending between the proximal end and the distal end of the catheter adapter body;
a compression resistant septum comprising a distal end formed in the compliant material of the catheter adapter body, the compression resistant septum further comprising a proximal end, wherein the distal end of the compression resistant septum and the catheter adapter body are integrally formed of the same compliant material, the compression resistant septum disposed toward the proximal end of the catheter adapter body the compression resistant septum comprising a lumen formed by the proximal end of the needle during the self-slitting process as the catheter adapter is assembled; and
a compression cap coupled to the proximal end of the compression resistant septum to the catheter adapter body and impart a radial compression force to the compression resistant septum such that the lumen narrows and seals when the needle is removed from the lumen.

10. The compliant catheter adapter of claim 9, wherein the compliant material comprises a thermoplastic elastomer material, a liquid silicone rubber material, or a polyisoprene material.

11. The compliant catheter adapter of claim 9, wherein the compression cap is positioned within at least a portion of the proximal end of the catheter adapter body, the compression cap further comprising:
a proximal end having a first aperture configured to receive the needle there through;
a distal end having a second aperture configured to receive at least a portion of the catheter adapter body; and
a compression surface extending intermediate the proximal end and the distal end of the compression cap, the compression surface enclosing a hollow portion formed in the compression cap, the hollow portion configured to receive the compression resistant septum therein, and the compression surface configured to impart the radial compression force to the compression resistant septum such that the lumen narrows and seals when the needle is removed from the lumen.

12. The compliant catheter adapter of claim 9, further comprising:
one or more stabilization members coupled to the catheter adapter body and configured to stabilize the catheter adapter body with respect to a patient;
a port in fluid communication with the inner chamber and configured to receive an extension tube, and the port comprising one of a Y-shaped port, a T-shaped port, a V-shaped port, and a parallel-shaped port;
a catheter lumen coupled to and extending from the distal end of the catheter adapter body; and
a catheter wedge disposed toward the distal end of the catheter adapter body and configured to guide the needle into the catheter lumen as the needle is inserted through the catheter adapter body.

13. The compliant catheter adapter of claim 9, wherein the compression resistant septum is a first compression resistant septum, further comprising a second compression resistant septum disposed within the inner chamber of the catheter adapter body, the second compression resistant septum positioned to abut the first compression resistant septum, wherein a septum chamber is formed between the first compression resistant septum and the second compression resistant septum, the second compression resistant septum having a second lumen formed by the proximal end of the needle during the self-slitting process as the catheter adapter is assembled.

14. The compliant catheter adapter of claim 9, wherein the compression cap is a separate piece that is coupled to the compression resistant septum and the catheter adapter body.

15. The compliant catheter adapter of claim 9, wherein the compression cap is coupled to the compression resistant septum and the catheter adapter body through an overmolding manufacturing process.

16. A catheter system comprising:
a needle component including:
a needle hub;
a needle coupled to the needle hub and extending distally from the needle hub, the needle comprising:
a proximal end, the proximal end of the needle shaped to facilitate a self-slitting/self-guiding process during assembly of the catheter adapter;
a distal end; and
a plurality of openings disposed along the needle between the proximal end and the distal end of the needle, wherein the plurality of openings are configured to facilitate flashback visualization; and
a grip coupled to the needle hub;
a catheter adapter body formed of a compliant material, the catheter adapter body comprising:
a proximal end and a distal end, the catheter adapter body having a generally elongate shape formed about a longitudinal axis extending between the proximal end and the distal end of the catheter adapter body;
an inner chamber disposed within the catheter adapter body, the inner chamber having a generally elongate shape formed about the longitudinal axis extending between the proximal end and the distal end of the catheter adapter body; and
a compression resistant septum comprising a distal end formed in the compliant material of the catheter adapter body, the compression resistant septum further comprising a proximal end, wherein the distal end of the compression resistant septum and the catheter adapter body are integrally formed of the same compliant material, the compression resistant septum disposed toward the proximal end of the catheter adapter body and comprising a lumen formed by the proximal end of the needle during the self-slitting process as the catheter adapter is assembled; and
a compression cap coupled to the proximal end of the compression resistant septum, the compression cap configured to impart a radial compression force to the compression resistant septum such that the lumen narrows and seals when the needle is removed from the lumen.

17. The catheter system of claim 16, wherein the grip coupled to the needle hub further comprises one of a paddle grip, a straight grip, and a ported grip.

18. The catheter system of claim 16, wherein the catheter adapter body is integrally formed from a compression set resistant elastomeric material comprising one of a thermoplastic elastomer material, a liquid silicone rubber material, and a polyisoprene material.

19. The catheter system of claim 16, wherein the compression cap further comprises:
- a proximal end having a first aperture configured to receive the needle there through;
- a distal end having a second aperture configured to receive at least a portion of the catheter adapter body; and
- a compression surface extending intermediate the proximal end and the distal end of the compression cap, the compression surface enclosing a hollow portion formed in the compression cap, the hollow portion configured to receive at least a portion of the compression resistant septum therein, and the compression surface configured to impart the radial compression force to the compression resistant septum such that the lumen narrows and seals when the needle is removed from the lumen.

20. The compliant catheter adapter of claim 1, wherein a majority or substantially all of the compression resistant septum is disposed within the compression cap.

* * * * *